(12) United States Patent
Nicolson et al.

(10) Patent No.: US 10,421,943 B2
(45) Date of Patent: *Sep. 24, 2019

(54) PHOSPHOLIPID COMPOSITIONS AND USE THEREOF TO ENHANCE SPERMATOZOA MOTILITY, VIABILITY AND RESISTANCE TO OXYDATIVE DAMAGE

(71) Applicant: ALLERGY RESEARCH GROUP, LLC, Alameda, CA (US)

(72) Inventors: Garth Nicolson, Huntington Beach, CA (US); Gonzalo Ferreira de Mattos, Montevideo (UY); Robert A. Settineri, Irvine, CA (US)

(73) Assignee: Allergy Research Group, LLC, Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/865,153

(22) Filed: Jan. 8, 2018

(65) Prior Publication Data

US 2018/0208889 A1  Jul. 26, 2018

Related U.S. Application Data

(63) Continuation-in-part of application No. 15/256,245, filed on Sep. 2, 2016, now Pat. No. 9,861,656, and a continuation-in-part of application No. 14/815,841, filed on Jul. 31, 2015, now Pat. No. 9,468,668, which is a continuation-in-part of application No. 14/152,938, filed on Jan. 10, 2014, now Pat. No. 9,095,507, which is a continuation-in-part of application No. 13/208,255, filed on Aug. 11, 2011, now Pat. No. 8,877,239, application No. 15/865,153, which is a continuation-in-part of application No. 15/295,878, filed on Oct. 17, 2016, now Pat. No. 9,717,734, which is a continuation-in-part of application No. 14/815,841, which is a continuation-in-part of application No. 14/152,938, which is a continuation-in-part of application No. 13/205,255, application No. 15/865,153, which is a continuation-in-part of application No. 15/662,212, filed on Jul. 27, 2017, now Pat. No. 10,117,885, which is a continuation-in-part of application No. 15/295,878, which is a continuation-in-part of application No. 14/815,841, which is a continuation-in-part of application No. 14/152,938, which is a continuation-in-part of application No. 13/208,255.

(60) Provisional application No. 62/245,868, filed on Oct. 23, 2015, provisional application No. 62/216,269, filed on Sep. 9, 2015, provisional application No. 61/750,991, filed on Jan. 10, 2013.

(51) Int. Cl.
*C12N 5/076* (2010.01)

(52) U.S. Cl.
CPC .......... *C12N 5/061* (2013.01); *C12N 2500/36* (2013.01); *C12N 2500/76* (2013.01); *C12N 2501/90* (2013.01); *C12N 2501/999* (2013.01)

(58) Field of Classification Search
CPC .. A61K 2300/00; A61K 31/07; A61K 31/201; A61K 31/205; A61K 31/355; A61K 31/375; A61K 31/685; A61K 31/733; A61K 33/04; A61K 33/30; A61K 31/661; A61K 31/683; A61K 31/70; C12N 2501/90; C12N 2501/999; C12N 5/061; C12N 2500/05; C12N 2500/32; C12N 2500/34; C12N 2500/38; C12N 2500/36; C12N 2500/76

See application file for complete search history.

(56) References Cited

U.S. PATENT DOCUMENTS

| 5,989,583 A * | 11/1999 | Amselem | A61K 9/145 424/439 |
| 2006/0257490 A1* | 11/2006 | Cremer | A23J 7/00 424/489 |

* cited by examiner

*Primary Examiner* — Mark V Stevens
(74) *Attorney, Agent, or Firm* — M.J. Ram and Associates; Michael J. Ram

(57) ABSTRACT

Sperm mobility and impregnation of an oocyte is enhanced by placing sperm in an aqueous solution of phospholipids prior to in vitro fertilization or artificial insemination. The aqueous phospholipid solution can also be used during storage or cryopreservation of the sperm. Also, the motility of sperm produced or ejaculated and the environment into which it is placed is enhanced my ingestion of the phospholipid composition by the male or female, or a vaginal placement of compositions containing the phospholipids.

9 Claims, 26 Drawing Sheets
(5 of 26 Drawing Sheet(s) Filed in Color)

| SPERM VELOCITY CHARACTERISTICS | | | | | |
|---|---|---|---|---|---|
| | | | PROGRESSIVE | MEDIUM PROGRESSIVE | FAST PROGRESSIVE |
| MEAN AMPLITUDE OF LATERAL HEAD DISPLACEMENT | ALH ($\mu$M) | CONTROL | 2.2 | 1.4 | 2.3 |
| | | 1%NTFL | 10.1 | 5.3 | 10.6 |
| BEAT CROSS FREQUENCY | BCF (Hz) | CONTROL | 2.5 | 1.7 | 2.9 |
| | | 1%NTFL | 10.5 | 7.2 | 13.6 |

FIG. 5

| MEAN SPERM HEAD SIZE | | | | | | |
|---|---|---|---|---|---|---|
| | | TOTAL | STATIC | SLOW | MEDIUM | FAST |
| SPERM HEAD AREA ($\mu^2$) | CONTROL | 16.2 | 16.8 | 16.9 | 14.6 | 14.1 |
| | 1%NTFL | 18.8 | 19.2 | 19.2 | 18.8 | 18.2 |

FIG. 6

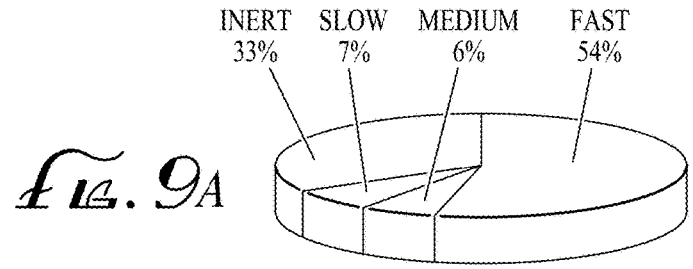
FIG. 9A
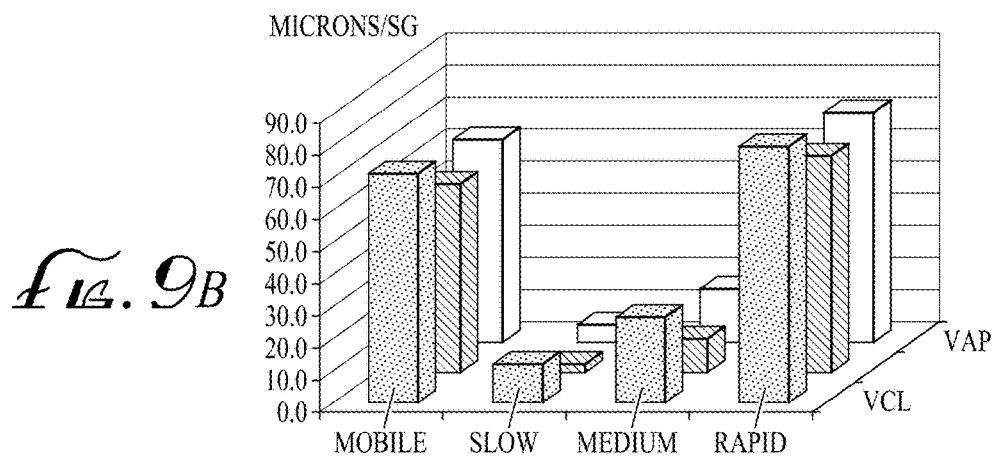
FIG. 9B
| SPERM VELOCITY CHARACTERISTICS (CENTRIFUGED) | | | PROGRESSIVE | MEDIUM PROGRESSIVE | FAST PROGRESSIVE |
|---|---|---|---|---|---|
| MEAN AMPLITUDE OF LATERAL HEAD DISPLACEMENT | ALH (μM) | CONTROL | 2.2 | 1.4 | 2.3 |
| | | 0.1%NTFL | 2.35 | 1.5 | 2.6 |
| BEAT CROSS FREQUENCY | BCF (Hz) | CONTROL | 10.2 | 5.3 | 10.6 |
| | | 0.1%NTFL | 10.2 | 6.9 | 12.7 |
FIG. 10

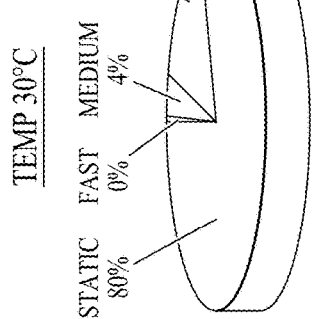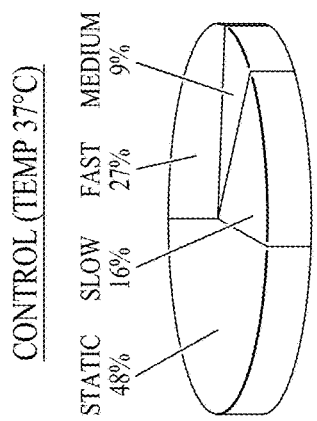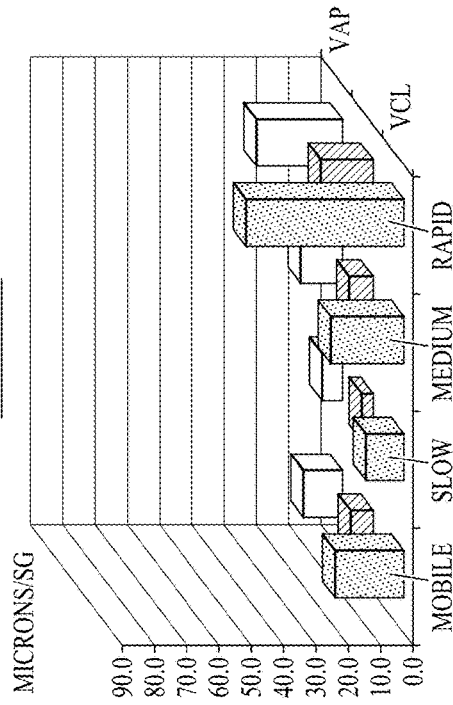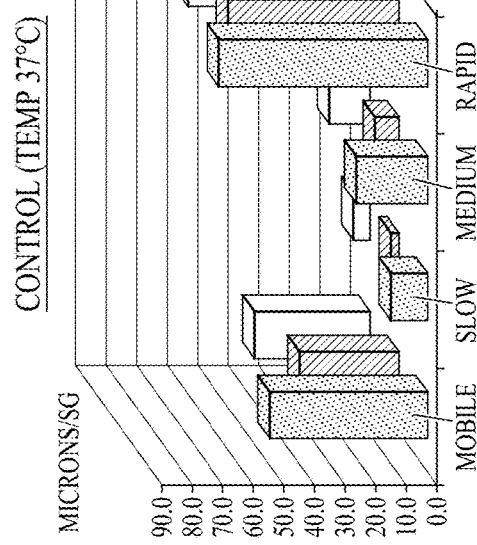

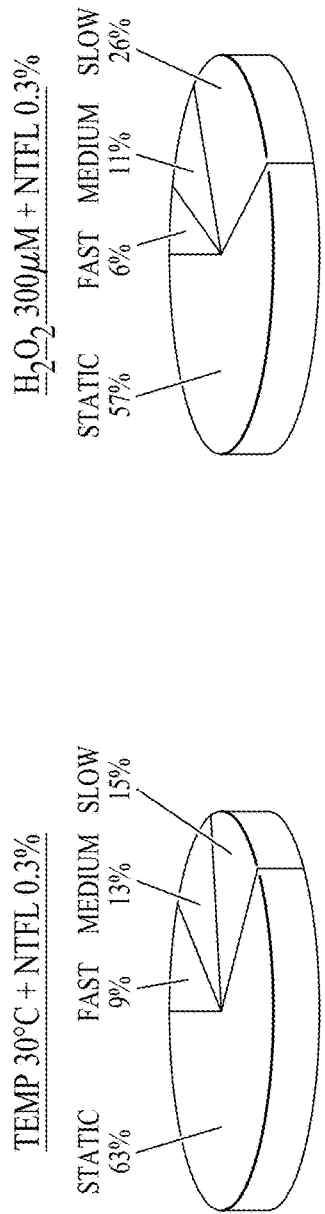
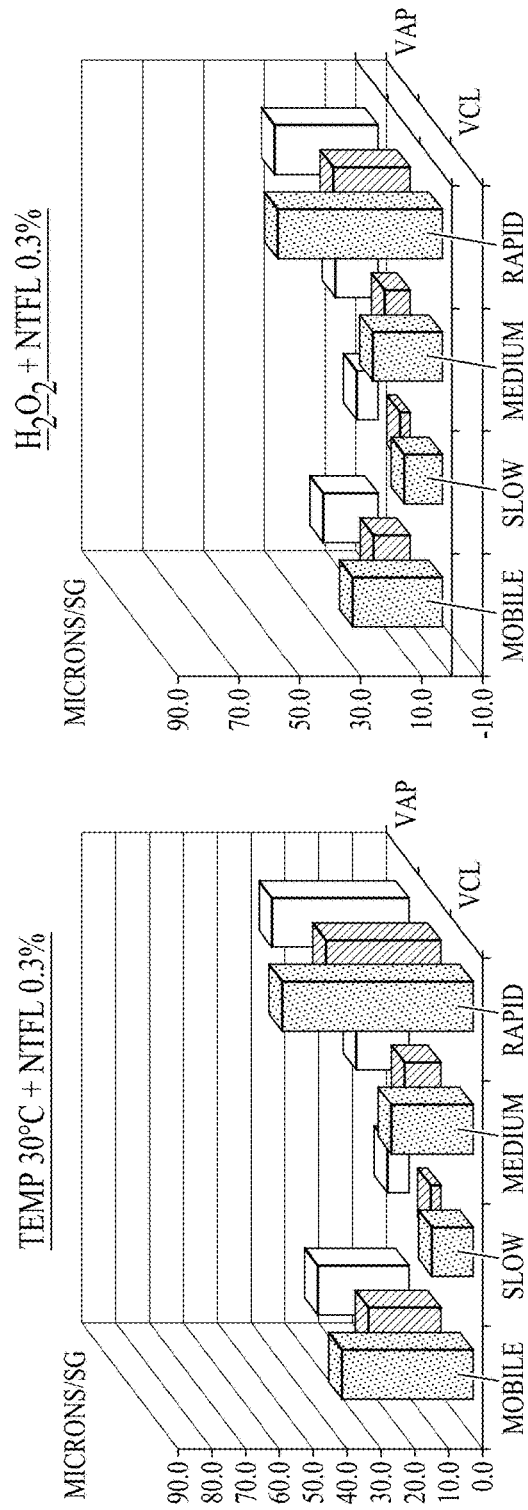

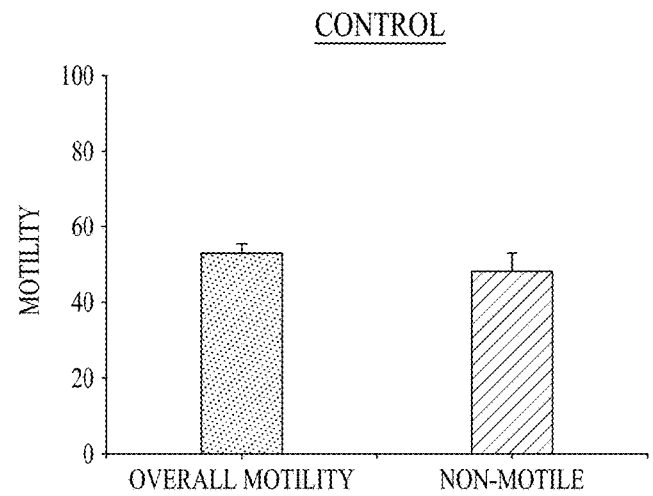
FIG. 19A1
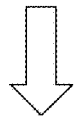
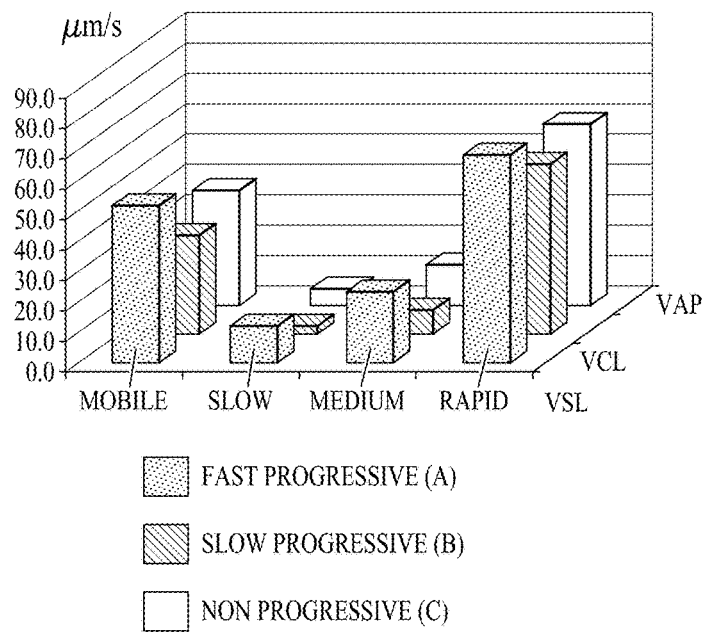
FIG. 19A2

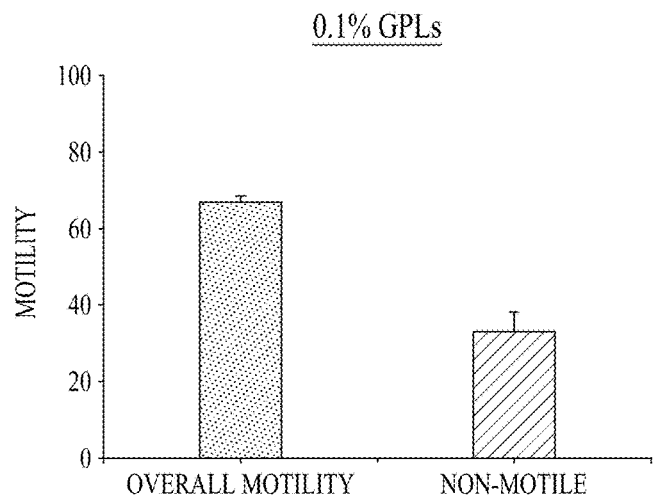
*fig.19B1*
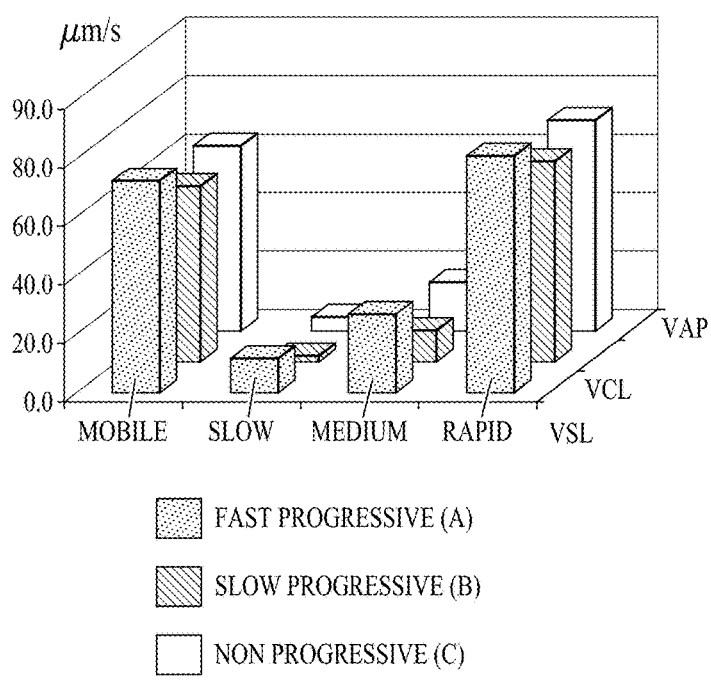
*fig.19B2*

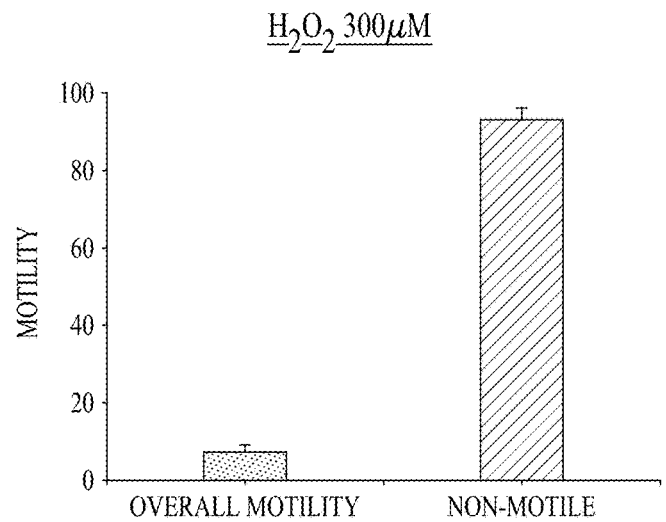
fig.19C1
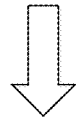
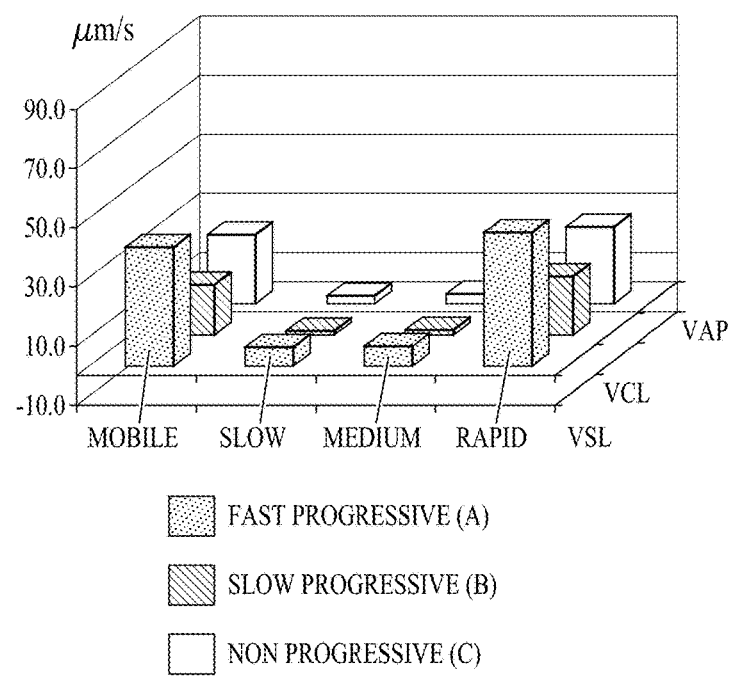
fig.19C2

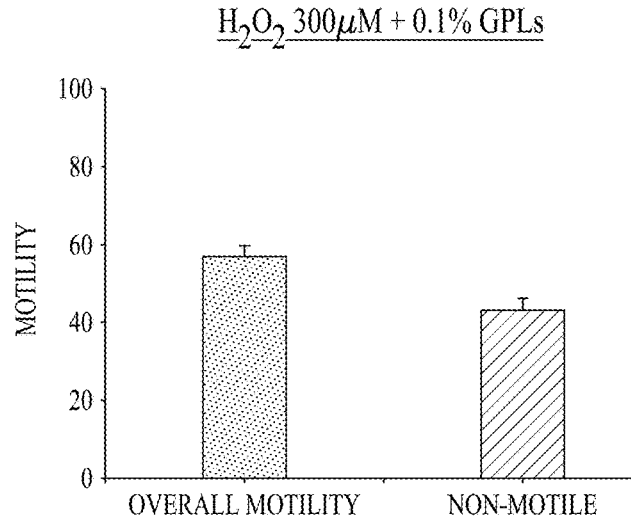
FIG. 19D1
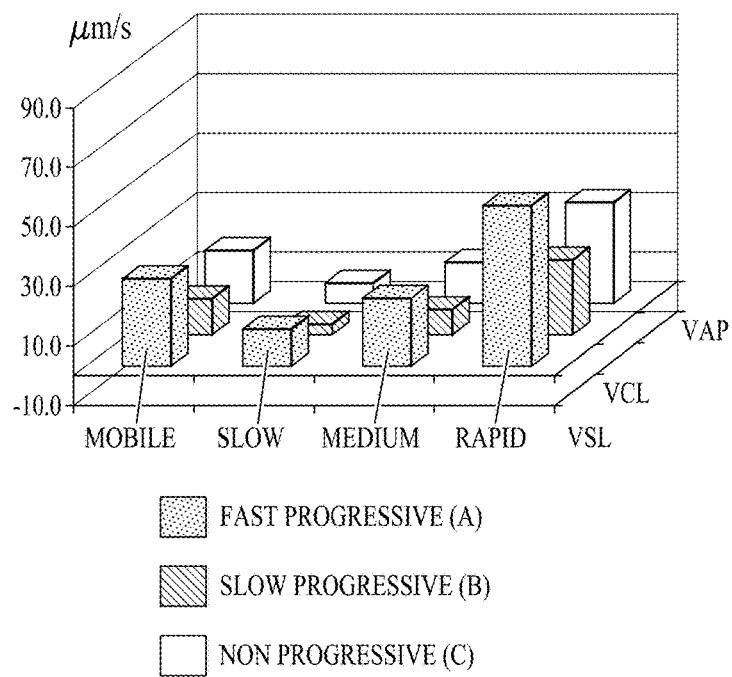
FIG. 19D2

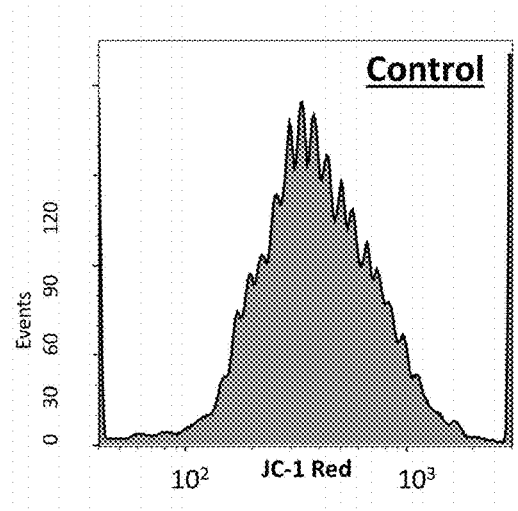
FIG. 22A1
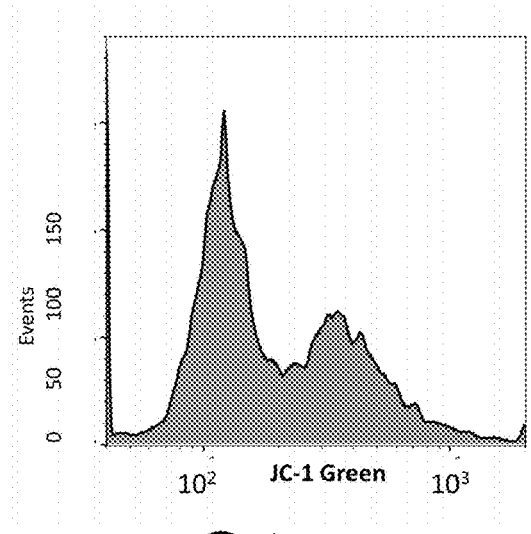
FIG. 22A2
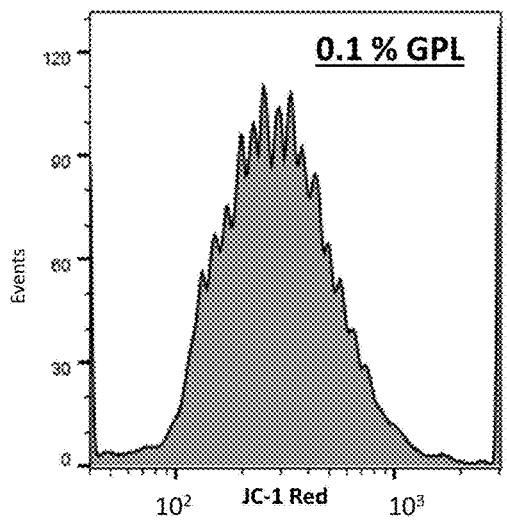
FIG. 22B1
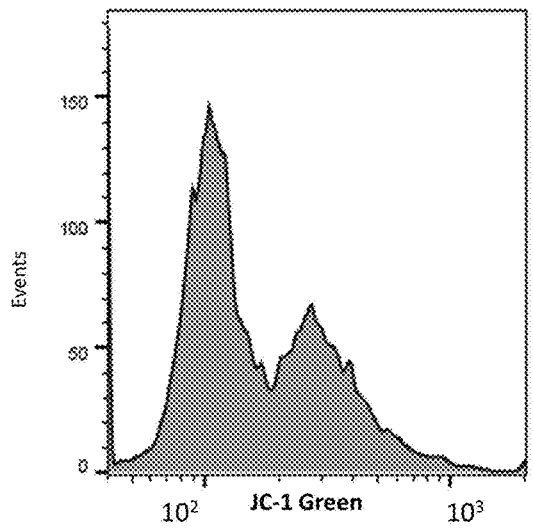
FIG. 22B2

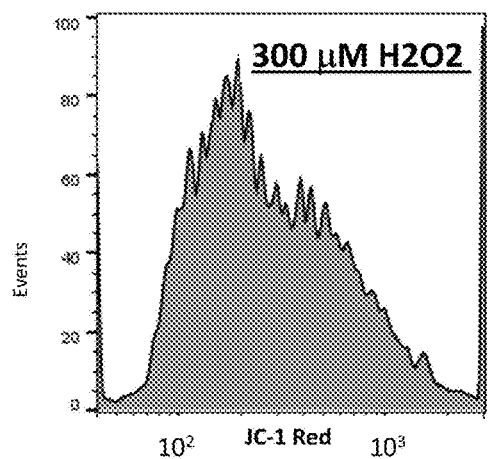
fig. 22C1
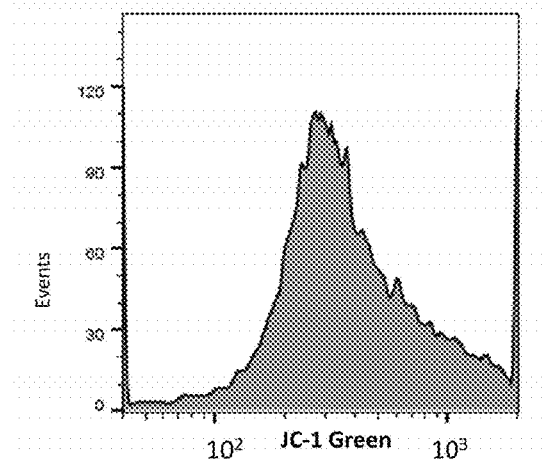
fig. 22C2
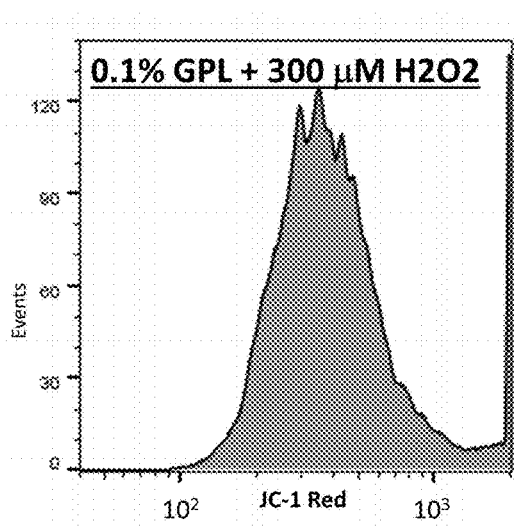
fig. 22D1
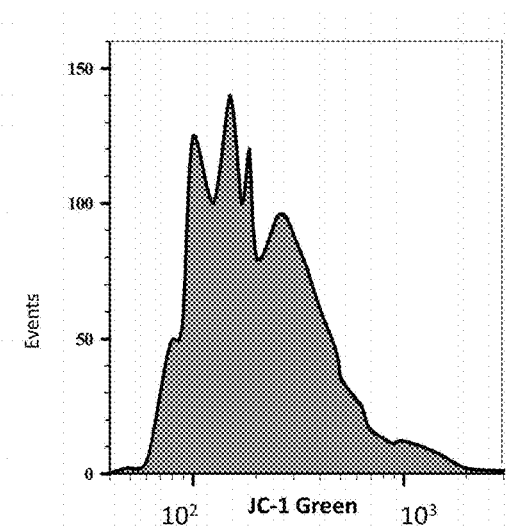
fig. 22D2

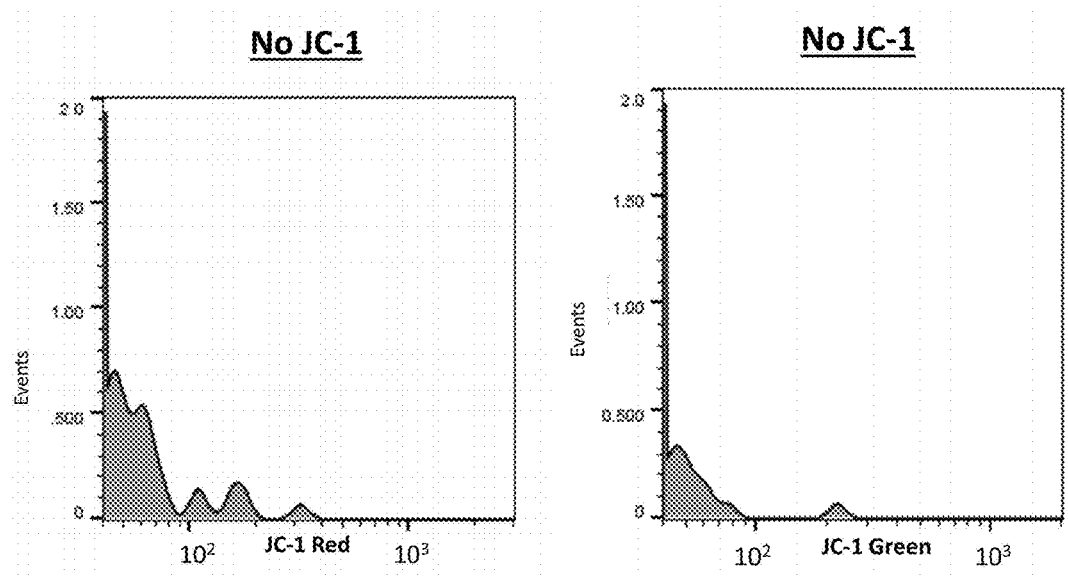
FIG. 22E1    FIG. 22E2
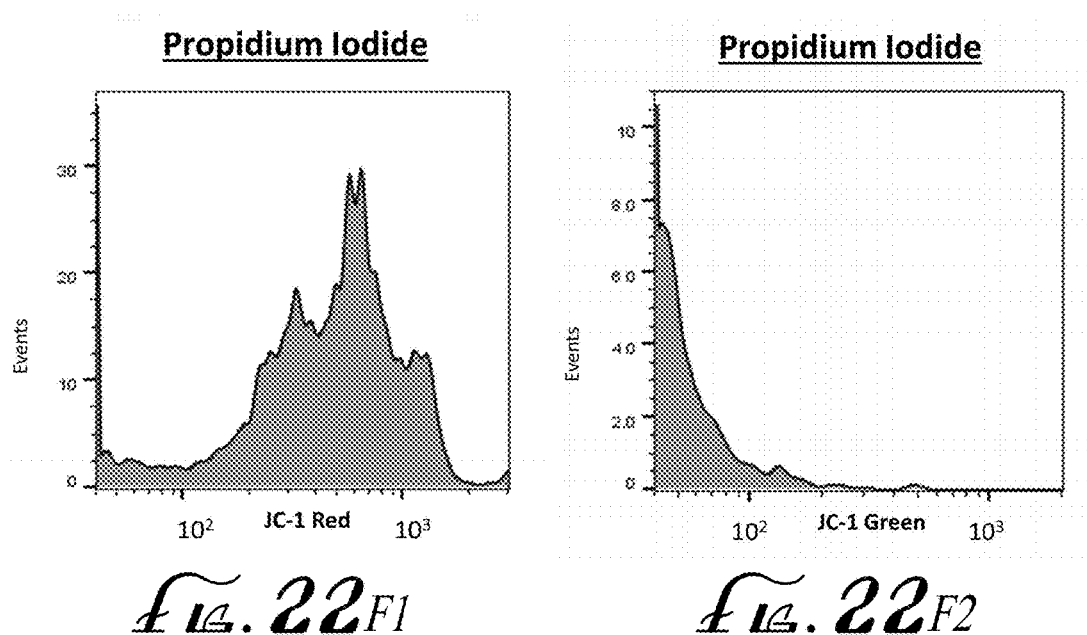
FIG. 22F1    FIG. 22F2

Control

Peaks Ratio Red/Green = 250/100 = 2.5

0.1 % GPLs

Peaks Ratio Red/Green = 210/80 = 2.6

300 µM H2O2

Peaks Ratio Red/Green = 80/130 = 0.62

300 µM H2O2 + 0.1% GPLs

Peaks Ratio Red/Green = 240/140 = 1.71

PHOSPHOLIPID COMPOSITIONS AND USE THEREOF TO ENHANCE SPERMATOZOA MOTILITY, VIABILITY AND RESISTANCE TO OXYDATIVE DAMAGE

CROSS REFERENCE TO RELATED APPLICATIONS

This application is a continuation-in-part of U.S. patent application Ser. No. 15/256,245 filed Sep. 2, 2016, now U.S. Pat. No. 9,861,656, issued Jan. 9, 2018, which claims benefit U.S. Provisional Application 62/245,868 filed Oct. 23, 2015 and U.S. Provisional Application 62/216,269 filed Sep. 9, 2015, both entitled PHOSPHOLIPID COMPOSITIONS AND USE THEREOF TO ENHANCE SPERMATOZOA MOTILITY AND VIABILITY. The present application is a CIP of U.S. patent application Ser. No. 14/815,841 filed Jul. 31, 2015, now U.S. Pat. No. 9,468,668 (the '668 patent) which is a CIP of U.S. patent application Ser. No. 14/152,938 filed Jan. 10, 2014, now U.S. Pat. No. 9,095,507 (the '507 patent) issued Aug. 4, 2015, which is a CIP of U.S. patent application Ser. No. 13/208,255 filed Aug. 11, 2011, now U.S. Pat. No. 8,877,239 (the '239 patent) issued Nov. 4, 2014. The present application is also a CIP of U.S. patent application Ser. No. 15/295,878 filed Oct. 17, 2016, now U.S. Pat. No. 9,717,734, issued Aug. 1, 2017, which is a CIP of U.S. patent application Ser. No. 14/815,841 filed Jul. 31, 2015, now U.S. Pat. No. 9,468,668, issued Oct. 18, 2016, which is a CIP of U.S. patent application Ser. No. 14/152,938 filed Jan. 10, 2014, now U.S. Pat. No. 9,095,507, issued Aug. 4, 2015, which is a CIP of U.S. patent application Ser. No. 13/208,255 filed Aug. 11, 2011, now U.S. Pat. No. 8,877,239, issued Nov. 4, 2014, and claims benefit of U.S. Provisional Application 61/750,991 filed Jan. 10, 2013. This present application is also a CIP of U.S. patent application Ser. No. 15/662,212 filed Jul. 27, 2017, which is a CIP of U.S. patent application Ser. No. 15/295,878 filed Oct. 17, 2016, now U.S. Pat. No. 9,717,734, issued Aug. 1, 2017, which is a CIP of U.S. patent application Ser. No. 14/815,841 filed Jul. 31, 2015, now U.S. Pat. No. 9,468,668, issued Oct. 18, 2016, which is a CIP of U.S. patent application Ser. No. 14/152,938 filed Jan. 10, 2014, now U.S. Pat. No. 9,095,507, issued Aug. 4, 2015, which is a CIP of U.S. patent application Ser. No. 13/208,255 filed Aug. 11, 2011, now U.S. Pat. No. 8,877,239, issued Nov. 4, 2014, and claims benefit of U.S. Provisional Application 61/750,991 filed Jan. 10, 2013, all hereby incorporated herein in their entirety by reference, including the drawings, charts, schematics, diagrams and related written description.

BACKGROUND

Field of the Invention

The present invention relates to methods for maintaining or enhancing sperm motility, counteracting the effects of aging and exposure to environmental factors that can reduce sperm motility, and providing a more friendly environment in the womb or in vitro and in turn increase the likelihood of fertilization of oocytes through vaginal or in vitro insemination. It also relates to preservation of mammalian sperm for human and animal insemination, for example in livestock breeding.

Mature mammalian, particularly human, spermatozoa are motile and survive for a few hours outside the male body. Signaling and motility processes must remain functional for sperm to be able to fertilize female gametes. Sperm membrane integrity is essential in maintaining spermatozoa viability and motility. While the results and conclusions set forth herein were obtained using mature human sperm, it is believed that the results and conclusions are likewise relevant to other mammalian spermatozoa and the results and conclusions set forth herein are applicable to mammalian sperm obtained from other than a human. Human sperm are highly sensitive to oxidative stress. Important targets of this process are cellular membranes, among other cellular components. Membrane Lipid Replacement (MLR) with glycerophospholipids (GPLs), has been found to repair oxidative damage to cellular membranes and prevent loss of function. The effects of MLR on sperm were tested by tracking and monitoring GPL incorporation into human sperm membrane systems and studying the effects on sperm motility and viability under different conditions are addressed herein. The results show that incubation of human spermatozoa with mixtures of exogenous, unoxidized GPLs results in their incorporation into sperm membranes, as shown by the use of fluorescent dyes attached to GPLs. Changes in sperm motility occurred concomitant with replacement of sperm membrane GPLs. When spermatozoa are damaged by oxidizing agents (such as hydrogen peroxide), the mitochondrial inner membrane potential (MIMP), monitored using MIMP tracker dyes like JC-1, diminishes. The addition of the GPL mixture prevented the decrease in MIMP. Confocal microscopy confirmed the mitochondrial localization of the dyes. The results confirm that incubation of human spermatozoa with mixtures of GPL, referred to herein as NTFL phospholipids, resulted in incorporation of these phospholipids into the membranes of spermatozoa. The replacement of sperm membrane GPLs improved their viability, motility and enabled them to resist oxidizing agents like $H_2O_2$, suggesting that sperm, and particularly human spermatozoa is a good model to test innovative new treatments like MLR. Such treatments can improve male fertility when it is adversely affected by increased oxidative stress.

DESCRIPTION OF THE RELATED ART

Sperm motility is a crucial factor for successful fertilization of oocytes (i.e., conception). The composition of the plasma membrane of the sperm is one the factors influencing sperm motility. The effects of aging, exposure to oxidative entities and changes in membrane lipid composition are important factors affecting male fertility. It has also been shown that changes in sperm membrane lipid composition are important factors resulting in a reduction in motility and the likelihood of fertilization. Peroxidation of the membrane lipids is also an important factor affecting for sperm health in adult life and as an individual ages.

The sperm cell has a unique structure and function. The sperm cell is viable in a body different from its origin, namely a female body, and is capable of navigating through the vagina and uterus to fertilize an egg released from the ovaries. The plasma membrane of the sperm cell also has a lipid composition different from most other cell membranes. It contains high amounts of polyunsaturated fatty acids (PUFA), particularly diPUFA (phospholipids esterified with two PUFA). PUFA are known to contribute to membrane fluidity and flexibility. The specific membrane lipid composition of the sperm cell has been found to be important for specific sperm functions promoting the creation of microdomains with different fluidity, fusogenicity, and permeability characteristics required for the sperm to navigate to, and to penetrate and fuse with the oocyte.

Gametogenesis of human spermatozoa comprises several stages. Sperm mature to produce a highly specialized, motile cell that must traverse a changing environment to fertilize an oocyte. From the total number of sperm cells (200-600 million) found initially in an ejaculate, only 200-300 will come close to an egg, and from those only one will eventually produce a fertile egg. Each motile sperm is surrounded by a unique plasma membrane that constitutes a physical barrier to the outside, but inside sperm are a number of other membranes that separate various sperm organelles, include their mitochondria.

The membranes of spermatozoa (SM) are more than just an inert barrier system. Lipids in the membranes of spermatozoa, especially the glycerolphospholipids (GPLs), are disparate in different membrane regions and undergo compositional changes during sperm maturation. They also function as an energy storage system. During sperm maturation the continuity between the plasma membrane and intracellular organelle membranes changes. SM are particularly enriched in polyunsaturated fatty acids (PUFA). In sperm, GPLs and sphingomyelin are characterized by the presence of long-chain and very-long-chain PUFAs. Almost 30% of the fatty acids are PUFA with approximately 60% docosahexoenoic (DHA), with high amounts of desmosterol plasmalogens are also very important components in SM.

During normal sperm maturation there are several changes in lipid compositions that influence membrane-membrane connections, fluidity and mobility of lipids within the sperm membranes. The changes in lipid compositions in sperm membranes are essential for membrane fusion and are required for the bending of the membrane domains to be fused, recruiting proteins from membranes and cytosol, and other properties. SM also exert appropriate control over signal processing mediators, such as $Ca^{2+}$. Changes in SM lipid composition, such as reductions in PUFA compared to saturated lipids, can lead to infertility.

Lipids from different SMs are subject to exchange and renewal by various mechanisms, such as endocytosis, exocytosis, contacts between different membranes and non-membrane lipid vesicles and by non-vesicular lipid carrier trafficking. For example, the compositions of lipids in the membranes of spermatozoa were susceptible to compositional changes by the incorporation/fusion of nanoliposomes.

As in other cells, the membranes of spermatozoa are particularly sensitive to oxidative damage, especially from Reactive Oxygen Species (ROS) and Reactive Nitrogen Species (RNS, jointly referred to as ROS/RNS. The production of ROS/RNS in spermatozoa has been known for some time, and was found to be important in sperm function and viability. In addition, lipid peroxidation was found to affect membrane integrity, leading to the loss of cytosolic components and finally cell death. The high concentrations of PUFA in SM makes them highly susceptible to lipid peroxidation. More specifically, reductions in sperm motility have been associated with lipid peroxidation of SM, and the loss of sperm motility with time has been used as an indirect estimation of oxidative stress and rate of lipid peroxidation. Reductions in sperm motility caused by SM lipid peroxidation were also reported as an important factor in decreases in fertility.

The natural defense mechanisms of spermatozoa against lipid peroxidation are mostly superoxide dismutase (SOD) and the glutathione peroxidase/reductase (GPX/GRD) systems. Both are essential, but the SOD defense system seems to be more variable between human sperm samples. The GPX/GRD system appears to be limited by the glucose-6-phosphate dehydrogenase-catalyzed rate of production of NADPH. In addition, seminal plasma can also act as a natural scavenger against lipid peroxidation. These natural defense systems can be overloaded in pathological conditions, leading to deficiencies in male.

Oxidative stress and the generation of ROS/RNS also have an impact on sperm mitochondrial function. Oxidative stress and excess ROS/RNS increase the activity of mitochondrial proteins, such as BCL-2, which stimulates release of mitochondrial proapoptotic factors into the cytosol that activate caspases.

The integrity of the membranes of sperm mitochondria are also compromised when there is loss of mitochondrial inner membrane chemical/electrical potential (MIMP). There is a direct relationship between loss of MIMP and sperm viability. The loss of MIMP leads to the reduction of ATP production during cell respiration. If mitochondria can't use oxidative phosphorylation, this eventually results in cell death. The over-production of ROS/RNS reduces the ATP levels in mature spermatozoa. Thus, when mitochondria are affected by oxidative stress, there is a loss in MIMP and this is followed by alterations in many sperm functions, such as motility, viability and the ability to undertake fertilization.

Phospholipids are key constituents of the lipid fraction of the sperm cell membranes, with phosphatidylcholine, phosphatidylethanolamine, and sphingomyelin being the major components. The lipid and fatty acid composition of sperm cells differ for different animals and different species as well as for fertile and subfertile population of the same species. Therefore, while published data on non-human sperm viability may not be translatable to the performance or viability of human sperm, applicants contend that, based on the data obtained and reported herein using human sperm, appropriate phospholipid compositions for preserving sperm from other species can now be readily established.

It is known that cryopreservation can affect the sperm membrane of non-human sperm. Further, freezing and thawing results in lipid modifications and domains of the sperm head plasma membrane react differently to cryopreservation. Furthermore, some studies investigated the ability of sperm cells in boar and bull semen to take up lipid components or fatty acids from the surrounding environment during incubation in vitro.

(Vasquez and Roldan, 1997) and, furthermore, Buhr et al. (1999) suggested a link between successful cryopreservation of boar semen and a given mixture of lipids and fatty acids in the original diluent. Once again, a specific role for the lipids present in the diluent or exchanges with spermatozoa are indicated. The present data also indicate that there was not only an uptake of lipid by sperm cells but also that this uptake was related to the quality of fresh semen. Phospholipase activities may mediate this lipid metabolism, totally or in part (for review, see Roldan, 1998). Buhr et al. (1994) reported an increase in the content of phospholipids, and in particular of phosphatidylcholine, during the cryopreservation of boar spermatozoa in the presence of egg yolk. The exact role of yolk components has not yet been clarified. Phosphatidylcholine (also called lecithin) has been proposed as the protective component during freezing (Quinn et al., 1980) since it prevented ultrastructural damage and favoured the maintenance of motility and respiration (Simpson et al., 1987). In contrast, studies have shown that phosphatidylcholine had no effect on boar sperm damage (Pursel et al., 1973) and did not prevent motility loss during cold shock and storage at −58 C (Watson, 1981). Phosphatidylserine has also been proposed as a protective agent in the boar (Butler and Roberts, 1975; Foulkes, 1977). Cationic low density lipoprotein (LDL) of egg yolk, characterized by a specific lipid:protein ratio of 2.7, was found to be the most efficient in protecting bull spermatozoa against cold shock. The cationic protein moiety of the LDL complex bound strongly to the sperm plasma membrane, which is negatively charged, and the lipid moiety was responsible for the protective action. (Vishwanath, R., Shannon, P., Curson, B., "Cationic Extracts Of Egg Yolk And Their Effects On Motility, Survival And Fertilising Ability Of Bull Sperm). *Anim. Reprod. Sci.*, 29, pp 185-194 (1992); A Maldjian, F Pizzi, T M Gliozzi, "Changes In Sperm Quality And Lipid Composition During Cryopreservation Of Boar Semen."—*Reproduction*, 121(3), pp 395-401 (2001)).

The major problem associated with cryopreservation of sperm cells is the loss of viability as a result of the freezing and thawing process. Loss of viability is related to membrane leakiness which is induced by sperm phospholipids peroxidation.

Infertility issues impact approximately 15% of all couples trying to conceive. Male infertility is a contributing factor in about half of these cases and high concentrations of oxidative-stress-causing agents have been identified in 30-80% of infertile men. Studies on the delivery of vitamin supplements and amino acids show an enhancement of specific sperm parameters (count, morphology, motility). Some antioxidants such as these vitamin C, selenium, vitamin E, L carnitine, Vitamin A, zinc and grapeseed extract have been shown to promote healthy sperm count, sperm morphology, and sperm motility, while reducing oxidative damage from agents, free radicals, or biological interactions that causes oxidative stress. (Dawson E B et al. "Effects Of Ascorbic Acid On Male Fertility", *Ann NY Acad Sci*, 498: pp 312-23 (1987)).

SUMMARY

NT Factor Lipids (NTFL) are compositions containing inulin and purified membrane glycerolphospholipids, as set forth in U.S. Pat. No. 8,877,239 (the '239 patent), U.S. Pat. No. 9,095,507 (the '507 patent) and U.S. Pat. No. 9,468,668 (the '668 patent), all incorporated herein in their entirety by reference, are powerful nutrients for antioxidant therapy and cell membrane repair. The '239 patent describes the formulation and delivery of those phospholipids composition for maintaining or restoring cell and mitochondrial health in the human body, or a specific organ system within the human body, or treating a specific disease or phospholipid deficiency within human body, said composition comprising a mixture of phospholipids or phospholipid precursors including a suitable carrier medium, and particularly in the form of a tablet, capsule or powder. The '507 and '668 patents describe and claim delivery of the NTFL compositions in the form of a chewable wafer or tablet. However, those patents do not show or suggest that the phospholipid compositions, referred to herein as NTFL or NT Factor Lipids, when ingested by a male will enhance the environment within the reproductive organs or semen of the male so as to result in improved vitality and motility of sperm cells produce by that male. Those patents also do not show or suggest that the phospholipid compositions, when ingested by a female will enhance the environment within the female sexual organs or cervical mucus and as a result provide an improved environment to receive the sperm and enhance the sperm motility to increase the likelihood of conception. Nor do those patents show or suggest that the NTFL phospholipids in solution will provide a more suitable fertilization environment and enhanced sperm motility when used in cryopreservation, during in vitro fertilization or prior to or during normal sexual activity intended to result in oocyte fertilization.

Set forth herein are the results of incubation of mature spermatozoa from healthy human donors with solutions containing NTFL phospholipids. It has been found by applicants that exposure of spermatozoa to the NTFL phospholipids reduces and/or reverses damage to the exposed spermatozoa and increases sperm motility, particularly in the most mobile sperm, and the resultant increased likelihood of egg fertilization. While data on preservation of animal sperm may not be directly translatable to human, it has been found that human data appears to be relevant to preservation of sperm from livestock used in artificial insemination in animal breeding and similar benefits have been found.

Applicants have used dietary Membrane Lipid Replacement (MLR) to replace oxidized mitochondrial membrane lipids, improve MIMP, and restore function (Nicolson G L, Ellithorpe R. "Lipid replacement and antioxidant nutritional therapy for restoring mitochondrial function and reducing fatigue in chronic fatigue syndrome and other fatiguing illnesses". *Journal of Chronic Fatigue Syndrome.*; 13(1):57-68. (2006); Nicolson G L, Ash M E. "Membrane Lipid Replacement for chronic illnesses, aging and cancer using oral glycerolphospholipid formulations with fructooligosaccharides to restore phospholipid function in cellular membranes, organelles, cells and tissues. *Biochim Biophys Acta.*; 1859(9 Pt B):pp 1704-1724. (2017 September)). MLR utilizes mixtures of cell membrane GPLs, plus fructooligosaccharides for protection against oxidative, bile acid and enzymatic damage, in order to safely replace damaged, oxidized, membrane GPLs. In initial studies of MLR with GPLs, have been shown to improve human sperm motility and viability (C. Costa T G, G. Ferreira, G. L. Nicolson. "Lipid replacement with a membrane glycerolphospholipid formulation: enhancement of spermatoozoa motility and viability". *Functional and Medical Foods for Chronic Diseases: Bioactive Compounds and Biomarkers*, 18: pp 202-6. (2015)). Applicants have now examined the ability of nano-micelles prepared from GPLs, to modify human sperm membranes. Mature human spermatozoa were also evaluated with incorporated GPLs to see if they can be protected from the loss of motility and viability due to the effects of oxidative stress. Further, incubation of human spermatozoa with nano-micelles prepared from GPLs were evaluated for prevention of the loss of MIMP produced by oxidizing agents like hydrogen peroxide ($H_2O_2$). Based on the results it is concluded that human spermatozoa are a good model to test innovative new treatments like MLR and that such treatments also improve male fertility when it is adversely affected by increased oxidative stress.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 is a table comparing the mean amplitude of lateral head displacement and the beat cross frequency of sperm in both the control and following incubation in the 1% NTFL solution.

FIG. 6 is a table comparing the sperm head area ($\mu^2$) in both the control and following incubation in the 1% NTFL solution.

FIG. 9A is a pie cart and FIG. 9B is a bar chart illustrating the effect of a 0.1 NTFL solution on a centrifuged sample of sperm.

FIG. 10 is a table illustrating sperm velocity characteristics of centrifuged sperm samples after exposure to the 0.1% NTFL.

FIGS. 12A and 12B are pie charts illustrating the effect of low temperature on sperm motility.

FIGS. 12C and 12D are 3-dimensional bar charts also illustrating the effect of low temperature on sperm motility.

FIG. 14A is a pie chart illustrating that 0.3% NTFL ameliorates the reduction of motility caused by exposure to low temperature.

FIG. 14B is a pie chart illustrating that 0.3% NTFL also ameliorates the reduction of motility caused by exposure to oxidation.

FIG. 14C is a 3-dimensional bar chart also illustrating that exposure to 0.3% NTFL ameliorates the reduction of motility caused by exposure to low temperature.

FIG. 14D is a 3-dimensional bar chart also illustrating that exposure to 0.3% NTFL ameliorates the reduction of motility caused by exposure to $H_2O_2$.

FIGS. 19A1, 19A2, 19B1, 19B2, 19C1, 19C2, 19D1 and 19D2 are bar charts illustrate the motility of mature human spermatozoa from adult males under normal conditions (control), exposure to GLPs, and exposure to an oxidative agent without and with GLPs being present with the graphs showing the straight line velocity (VSL), curvilinear velocity (VCL) and average path velocity (VAP) for the various sperm classes.

FIG. 21A shows the results obtained after control incubation of spermatozoa; FIG. 21B illustrates incubation of sperm with 0.1% GPLs added; FIG. 21C illustrates incubation of sperm with 300 μM $H_2O_2$, FIG. 21D illustrates incubation of sperm with 300 μM $H_2O_2$ with the addition of 0.1% GPLs added, FIG. 21E illustrates the control obtained with unstained spermatozoa (without JC-1) and FIG. 21F shows cells stained with JC-1 and exposed to the toxic molecule PI.

FIGS. 22A1, 22A2, 22B1, 22B2, 22C1, 22C2, 22D1, 22D2, 22E1, 22E2, 22F1 and 22F2 show intensity histograms for red and green fluorescence of spermatozoa stained with JC-1. In each instance the left panel (FIGS. 22A1-22F1) is a histograms of the red fluorescence and right panel (FIGS. 22A2-22F2) represents the green fluorescence, each in a semi-log scale. FIGS. 22A1 and 22A2 shows the red and green fluorescence of the control. FIGS. 22B1 and 22B2 provides fluorescent histograms of sperm obtained after incubation with 0.1% GPLs. FIGS. 22C1 and 22C2 shows the fluorescent histograms of sperm obtained after incubation in 300 μM $H_2O_2$. FIGS. 22D1 and 22D2 are Fluorescent histograms of sperm cells after exposure to 300M $H_2O_2$ in the presence of 0.1% GPLs. FIGS. 22E1 and 22E2 show fluorescent histograms of sperm cells measuring intrinsic red and green fluorescence without JC-1. FIGS. 22F1 and 22F2 represents the fluorescent histograms of sperm cells in the presence of Propidium Iodide (PI).

FIG. 23B illustrates Spermatozoa stained with Rhodamine 123 in media containing 0.1% GPLs. FIG. 23C shows Spermatozoa stained with Rhodamine 123 in media containing 300 μM $H_2O_2$. FIG. 23D shows Spermatozoa stained with Rhodamine 123 in media containing 300 μM $H_2O_2$ with 0.1% GPLs.

FIG. 24A is a live imaging of spermatozoa incubated in control medium. FIG. 24B shows human spermatozoa stained with JC-1 in the presence of 0.1% GPLs. FIG. 24C shows Spermatozoa incubated in 300 μM $H_2O_2$. And FIG. 24D shows Spermatozoa co-incubated with 300 μM $H_2O_2$ and 0.1% NTFL. The graphs to the right of each of FIGS. 24A-24D illustrate the fluorescence intensity along the yellow segment in each figure.

DETAILED DESCRIPTION

Figure 1:
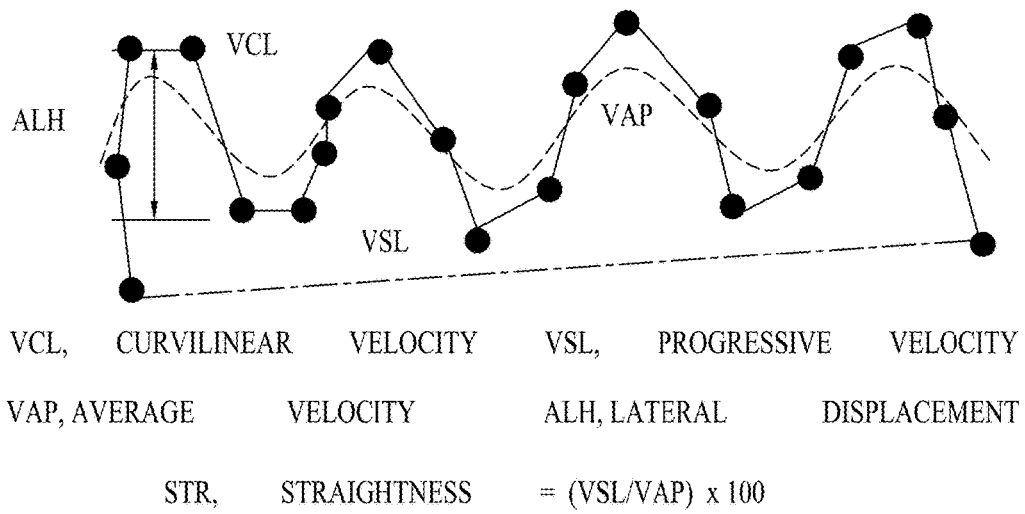
FIG. 1 illustrates the elements of sperm motility.

NTFL is a phospholipid composition described in U.S. patent application Ser. No. 13/208,255, issued as U.S. Pat. No. 8,887,259 incorporated in its entirety herein by reference. Said phospholipid composition comprises inulin and a mixture of phospholipids comprising phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid. In a preferred embodiment NTFL phospholipid components comprises 19-29% phosphatidylcholine (PC), 15-25% phosphatidylethanolamine (PE), 3.5%-10% phosphatidic acid (PA), 10-18% phosphatidylinositol (PI), 2-10% phosphatidylglycerol (PG),10-20% glycolipids, and 5-11% other phospholipids. This composition along with inulin was used in the studies herein. In another preferred composition mixture of phospholipids having about 25% to about 29% phosphatidylglycerol (PG), about 68% to about 72% phosphatidylcholine (PC), and up to about 5% phosphatidylethanolamine (PE), and may optionally include about 1% to about 5% phosphatidylinositol (PI) and phosphatidylserine (PS).

Based on data collected regarding the ability of aqueous solutions of NTFL compositions containing phospholipid to enhance sperm motility in vitro and the ability of ingested NTFL phospholipid compositions to improve mitochondrial heath and function throughout the body, enhanced sperm motility can be provided by delivering the NTFL composition to a male individual to create an enhanced phospholipid environment in said individual's semen or to a female to create an enhanced phospholipid environment in said female individual's vaginal fluids or cervical mucus. The NTFL composition can be delivered in the form of a tablet, capsule or powder as set forth in U.S. Pat. No. 8,877,239. In one embodiment the powdered NTFL may be incorporated in a food product or blended into a suitable liquid and consumed in the form of a beverage, which may be cold or heated. In the alternative, the NTFL powder may be formed into an edible wafer or tablet, for example by compaction in a tablet press such as described in U.S. Pat. Nos. 9,468,668 and 9,095,507 referred to above, or divisional or CIP applications thereof. In a still further embodiment the phospholipid mixture may be included in a vaginal suppository or vaginal lubricant, cream, jelly, foam or gel delivered prior to or directly after sexual intercourse, such as described below. Further, NTFL compositions containing phospholipids are also beneficial additives in solutions for collecting, storing and preserving (including cryopreservation) live spermatozoa from humans and animals for artificial insemination and in vitro fertilization. Addition of one or more antioxidants such as these vitamin C, selenium, vitamin E, L carnitine, Vitamin A, zinc and grapeseed extract to the NTFL phospholipid compositions are also beneficial in further enhancing the increase in sperm motility demonstrated by the use of NTFL.

Described below is an evaluation of the beneficial effect of NTFL phospholipid compositions on the motility of sperm and evidence that the NTFL composition passes through the cell membrane and positively enhances the phospholipid composition within the sperm cell and in the mitochondria. Increased sperm motility, all other factors remaining constant, will increase the likelihood of an oocyte being penetrated by the sperm, whether in vivo or in vitro, which in turn results in an enhanced likelihood of egg fertilization.

ComparativeTests.

For the data set forth below and shown in FIGS. 1-14A-D a first group of healthy human male participants aged 20 to 51 with no known infertility conditions donated sperm samples (n=12). Using the swim-up method the samples were treated to obtain viable spermatozoa. Multiple comparable portions of the viable spermatozoa were then collected for the comparative evaluations described below and were incubated under various different conditions for an average time of 2-3 h. Sperm samples were placed in control aqueous solutions of HamF10 (see Table 1) and HamF10 containing NTFL at several concentrations (0.1 to 3% g/ml) and incubated for periods of 1 to 4 hours in an incubator containing a 5% $CO_2$ atmosphere were compared.

The NTFL glycerolphospholipids, were found to be incorporated into the spermatozoa membranes in incubations of at least about two hours based on the correlation between sperm head area and NTFL %. After the incubation, the samples were centrifuged at low velocity (approximately 500-1000 RPM in a 10 cm centrifuge, preferably 800 RPM) and later observed in a Leja Chamber for examination with Computer Assisted Sperm Analysis (CASA) (Hirano Y, Shibahara H, Obara H, Suzuki T, Takamizawa S, et al. "Andrology: Relationships Between Sperm Motility Characteristics Assessed By The Computer-Aided Sperm Analysis (CASA) And Fertilization Rates In Vitro". J Assist Reprod Genet (2001); 18: 215-220). An average of 10 treatments at 37° C. were evaluated (SCA, Microptics). Other samples were treated at lower temperatures (24° C. or 30° C.), to test the effect of NTFL under stress conditions such as temperature. The same procedure was also performed with samples incubated at 37° C. with $H_2O_2$ as a chemical oxidative stress agent.

TABLE 1

| Ham's F10* | | | |
|---|---|---|---|
| Component | mg/lt | Mol. Wt. | Mol. (mM) |
| Amino Acids | | | |
| L-Alanine | 89.10000 | 89.1 | 1.00 |
| L-Arginine HCl | 2107.00000 | 174.2 | 12.10 |
| L-Asparagine H2O | 150.10000 | 150.1 | 1.00 |
| L-Aspartic Acid | 133.10000 | 133.1 | 1.00 |
| L-Cysteine HCl H2O | 351.30000 | 175.6 | 2.00 |
| L-Glutamic Acid | 147.10000 | 147.1 | 1.00 |
| Glycine | 75.10000 | 75.07 | 1.00 |
| L-Histidine HCl $H_2O$ | 209.60000 | 209.6 | 1.00 |
| L-Isoleucine | 26.20000 | 131.2 | 0.20 |
| L-Leucine | 131.20000 | 131.2 | 1.00 |
| L-Lysine HCl | 293.00000 | 182.6 | 1.60 |
| L-Methionine | 44.80000 | 149.2 | 0.30 |
| L-Phenylalanine | 49.60000 | 165.2 | 0.30 |
| L-Proline | 115.10000 | 115.1 | 1.00 |
| L-Serine | 105.10000 | 105.1 | 1.00 |
| L-Threonine | 35.70000 | 119.1 | 0.30 |
| L-Tryptophan | 6.10000 | 204.2 | 0.03 |
| L-Tyrosine | 18.10000 | 181.2 | 0.10 |
| L-Valine | 35.10000 | 117.1 | 0.30 |
| Vitamins | | | |
| Biotin | 0.24000 | 244.3 | 0.0010 |
| Choline Chloride | 6.98000 | 139.6 | 0.05 |
| D-Calcium Pantothenate | 7.15000 | 238.3 | 0.03 |
| Folic Acid | 13.20000 | 441.4 | 0.03 |
| myo-Inositol | 5.41000 | 180.2 | 0.03 |
| Nicotinamide | 6.11000 | 122.13 | 0.05 |
| Pyridoxine HCl | 2.06000 | 205.6 | 0.01 |
| Riboflavin | 3.76000 | 376.4 | 0.01 |
| Thiamine HCl | 10.12000 | 337.3 | 0.03 |
| Vitamin B12 | 13.60000 | 1355.4 | 0.01 |
| Inorganic Salts | | | |
| Calcium Chloride Dihydrate [CaCl2 2H2O] | 441.00000 | 147.0 | 3.00 |
| Cupric Sulfate [CuSO4] | 0.01600 | 159.68 | 0.0001 |
| Ferrous Sulfate Heptahydrate [FeSO4 7H2O] | 8.34 | 278.0 | 0.03 |
| Magnesium Sulfate [MgSO4] | 746.00000 | 120.4 | 6.20 |

TABLE 1-continued

Ham's F10*

| Component | mg/lt | Mol. Wt. | Mol. (mM) |
|---|---|---|---|
| Potassium Chloride [KCl] | 2850.00000 | 74.55 | 38.23 |
| Potassium Phosphate Monobasic [KH2PO4] | 830.00000 | 136.09 | 6.10 |
| Sodium Chloride [NaCl] | 74000.00000 | 58.44 | 1266.26 |
| Sodium Phosphate Dibasic [Na2HPO4] | 1562.00000 | 141.96 | 11.00 |
| Zinc Sulfate Heptahydrate [ZnSO4 7H2O] | 0.28800 | 287.5 | 0.0010 |
| Other | | | |
| Dextrose | 11000.00000 | 180.2 | 61.04 |
| Hypoxanthine | 40.80000 | 136.1 | 0.30 |
| Lipoic Acid | 2.06000 | 206.3 | 0.01 |
| Phenol Red Sodium Salt | 12.40000 | 376.4 | 0.03 |
| Sodium Pyruvate | 1100.00000 | 110.0 | 10.00 |
| Thymidine | 7.27000 | 242.2 | |

*Ham, R. G., Exptl. Cell Res., v. 39, 515 (1963).

FIG. 1 illustrates the elements of sperm motility where:
VCL—Curvilinear velocity—Velocity of sperm in a trajectory for progression
VSL—Progressive velocity—Velocity of sperm in an axis straight line for progression
VAP—Average velocity—Velocity measured on a mean sperm trajectory for progression. All velocities are measured in µM/s)
LIN—Linearity—Ratio of axis straight line and curved trajectory velocities (VSL/VCL)
STR—Straightness—Ratio of straight line and mean trajectory velocities (VSL/VAP)
WOB—Oscillation index—Oscillation of trajectory about an spatial average path. These indexes are expressed as %
ALH—Amplitude of the lateral displacement of the head from mean axis straight line (µM)
BCF—Beat Cross Frequency—Number of times per second that sperm crosses the Mean axis straight line (Hz).

FIG. 1 shows the characteristics of motility and velocity of human sperm (usually measured in micrometer/sec). The solid line curve (VCL) represents the actual curvilinear velocity or track of a single motile sperm cell, whereas the dashed line curve represents the average velocity (VAP) of many sperm cells. The movement consists of the amplitude of lateral movement or displacement (ALH) of the sperm head from a straight line and progressive (forward or straight-line) movement (VSL). The straightness velocity of movement (STR) can be defined as VSL/VAPX100. The figure illustrates all the motility parameters shown in the WHO manual on sperm studies to be relevant to fertility.

Figure 2:
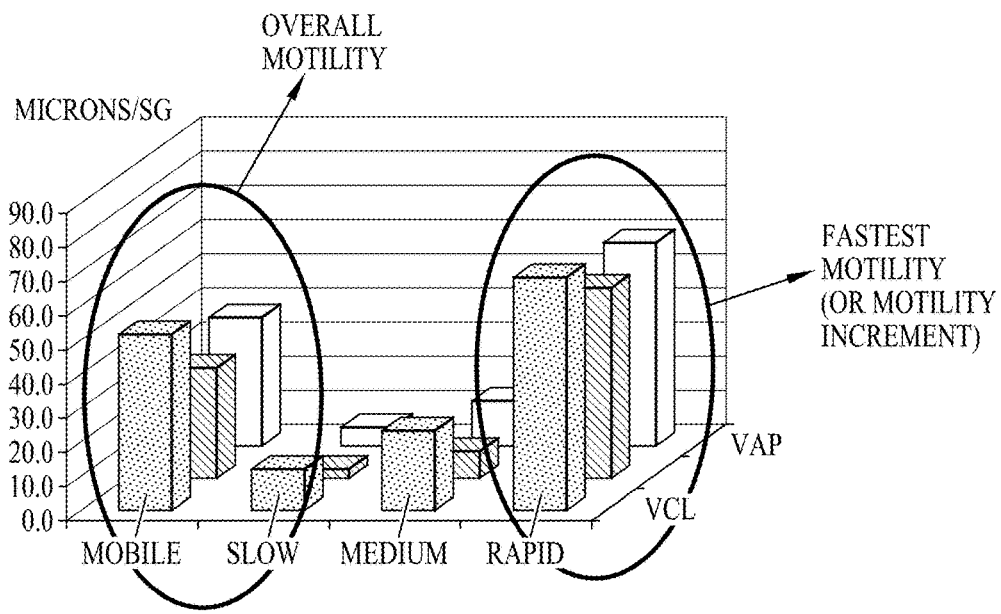
FIG. 2 is a graphical representation of the motility of human sperm.

FIG. 2 is a graphical representation showing the distribution of sperm motility in a typical collected sample (identified as mobile) with the sample broken down into three classifications, namely, slow, medium and rapid and, within each classification the curvilinear and average velocity.

The differences between those motilities, are explained in the WHO Laboratory Manual For Examination And Processing Of Human Semen (5th Edition), World Health Organization, (2010). According to the Manual, when discussing sperm motility, it is important to specify total motility (PR+NP) or progressive motility (PR). A simple system for grading motility is recommended that distinguishes spermatozoa with progressive or non-progressive motility from those that are immotile. The motility of each spermatozoon is graded as follows:
a. Progressive motility (PR): spermatozoa moving actively, either linearly or in a large circle, regardless of speed;
b. Non-progressive motility (NP): all other patterns of motility with an absence of progression, e.g. swimming in small circles, the flagellar force hardly displacing the head, or when only a flagellar beat can be observed; and
c. Immotility (IM): no movement.

The previous edition of this manual recommended that progressively motile spermatozoa should be categorized as rapid or slow, with a speed of >25_m/sec at 37° C. defining "grade a" spermatozoa. However, it is difficult for technicians to define the forward progression so accurately without bias (Cooper & Yeung, 2006).

FIG. 2 shows a typical experiment and the data that results from analysis of the various parameters of sperm motility showing an average motility (all motile or mobile sperm) and the sperm motility separated into several velocity categories specifically slow, medium and rapidly moving motile sperm.

Figure 3A:
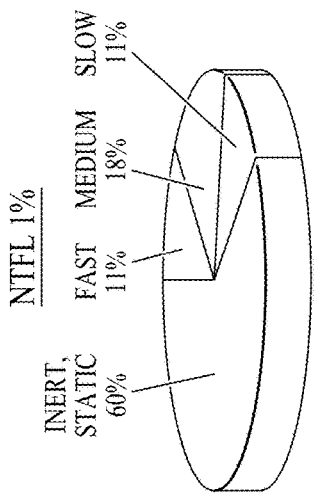
FIGS. 3A and 3B comprise two pie charts comparing the sperm velocity characteristics of a control sperm sample to the same sperm sample after exposure for 3 hours to a 1% NTFL concentration.
Figure 3B:
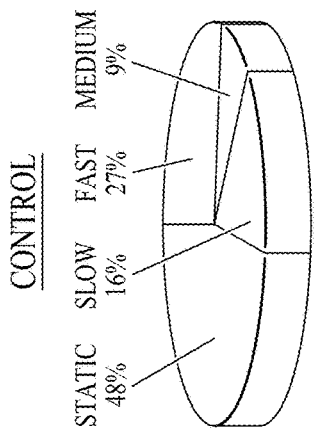

The pie charts in FIG. 3 show progressive motility as fast, medium and slow and non-progressive motility, immotile spermatozoa percentage (static). Slow progressive motility is represented by slow or medium mobile sperm. FIGS. 3A and 3B show the distribution of sperm activity for a control sperm sample (FIG. 3A) compared to the same sperm sample after exposure for 3 hrs to a 1% NTFL concentration (FIG. 3B). The data shows significant improvements in sperm motility but this can only be seen at lower NTFL concentrations where the NTFL micelles don't interfere with sperm motility as a result of impact of NTFL micelles with sperm. For example, in concentrations between 0.01 and 0.3%, particularly from 0.1-0.3%, sonicated, micro-emulsified NTFL samples sperm motility was increased. This was also found in sperm samples at the higher NTFL concentrations (1%) where the sperm were separated from the NTFL micelles by brief centrifugation. In other words, sperm motility was actually significantly increased in the sample with 1% NTFL, but the increase could not be properly measured due to the sperm collision with NTFL micelles.

Figure 4A:
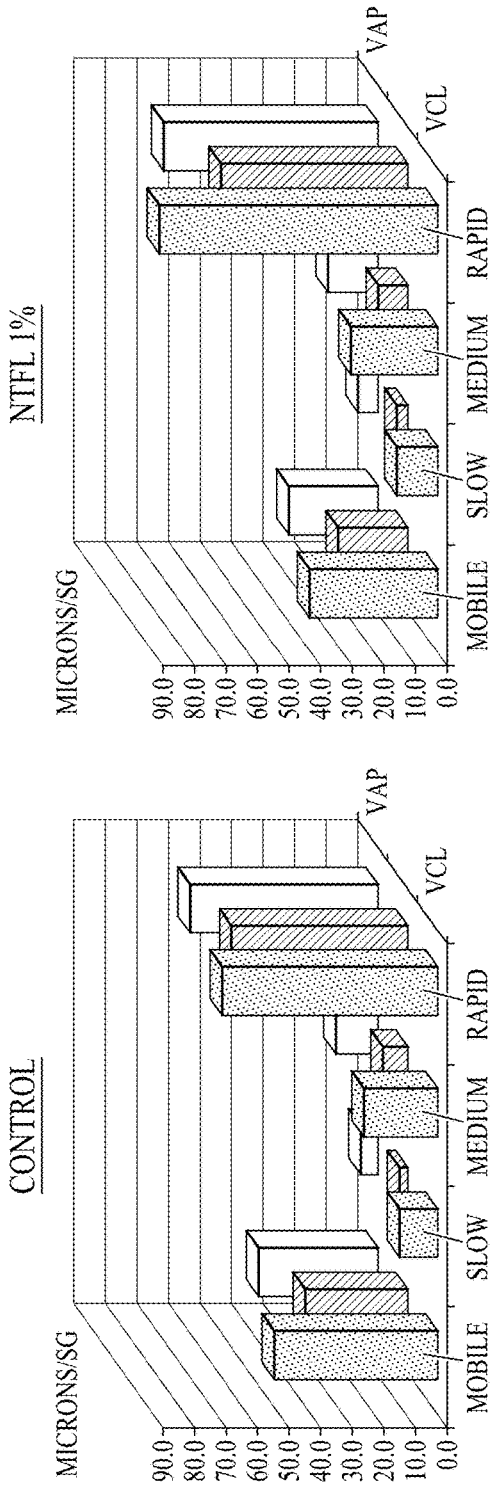
FIGS. 4A and 4B comprise two 3 axis bar charts comparing control sperm samples to 1% NTFL treated sperm.
Figure 4B:
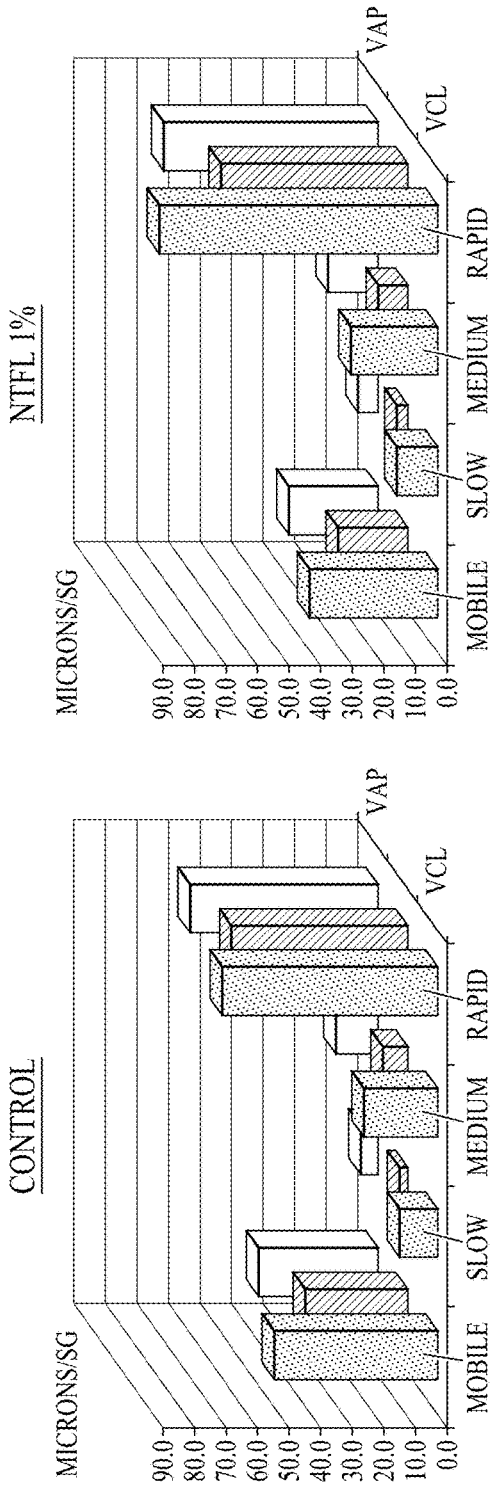

FIGS. 4A and 4B are 3 axis bar charts comparing the same control sperm samples to 1% NTFL treated sperm as in FIGS. 3A and 3B. At NTFL concentrations near 1% the overall velocities of sperm in the sample were reduced due to micelle collisions and motility interference. The bars in the right row of the chart illustrate mobile, rapidly moving sperm involved in collisions with relatively large lipid micelles. Motile sperm, however, had an average increase in velocities (VCL, VSL, VAP, LIN, STR, WOB) of 18±4% (p<0.05 independent t-test).

FIG. 5 is a table comparing the mean amplitude of lateral head displacement (ALH) and the beat cross frequency (BCF) of sperm in both the control and following incubation in the 1% NTFL solution. The presence of NTFL phospholipids increases ALH and BCF which are critical for fertility prediction in a sperm sample. These parameters related to flagella activity, especially BCF, which are indicative of the strength of penetration during fertility, were also increased by approximately the same amount and at the same significance level.

To test if the NTFL composition becomes incorporated into the sperm membrane, changes in the sperm head area were determined. FIG. 6 is a table comparing the sperm head area ($\mu^2$) in both the control and following incubation in the 1% NTFL phospholipid solution. A statistically significant increase in sperm head velocity was found to occur in all NTFL incubated sperm cells in the sample, indicating a significant incorporation of the NTFL into each sperm cell. Alternatively, it was found that a comparison of a 123 Rhodamine stained control sperm sample with a stained sperm sample in a NTFL 0.02% solution, even when exposed to 300 uM of $H_2O_2$, showed a significant increase in cytoplasmic droplets in spermatozoa in a confocal field of sperm seeded at the same concentration (an increase from 12% to 72%, $p<0.05$). 123 Rhodamine stains mostly mitochondrial membranes and plasma membrane regions in the midpiece, neck and subequatorial head of the sperm cell. Xu, Yuan et al. (2013) has pointed that the presence of cytoplasmic droplets is indicative of healthy and motile sperm (Hui Xu, Shui-Qiao Yuan, Zhi-Hong Zheng, and Wei Yan, "The Cytoplasmic Droplet May Be Indicative Of Sperm Motility And Normal Spermiogenesis", *Asian J Androl.* (2013 November); 15(6): 799-805).

Figure 7:
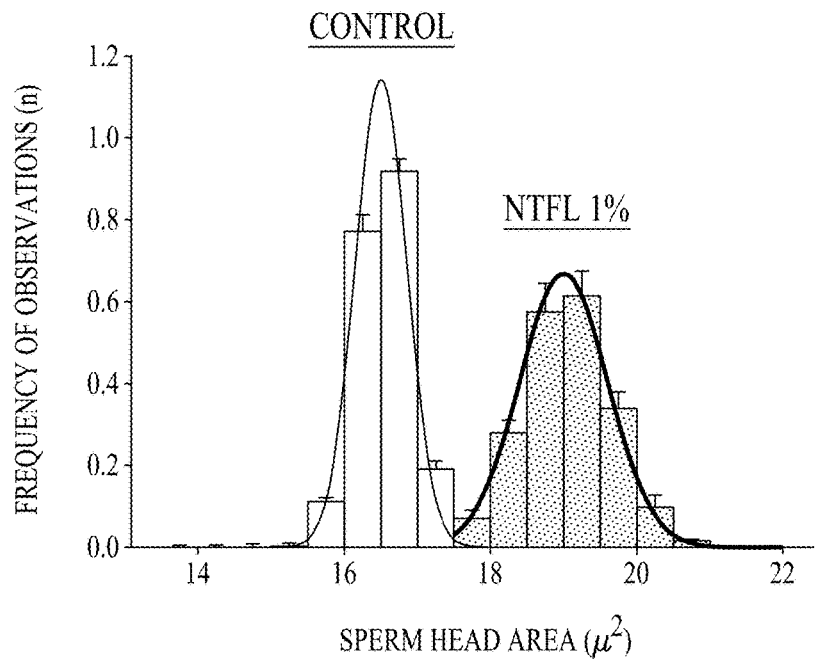
FIG. 7 is a graph comparing the normal distribution of sperm head size in the Control with the 1% NTFL incubated sample.

FIG. 7 is a graph comparing the normal distribution of sperm head size in control solutions with equivalent sperm samples incubated in a 1% NTFL solutions. The significant increase in sperm head area from an average of 16 μm in the Control to 19 μm in the NTFL solution ($p<0.05$, independent t-test) and a greater distribution thereof shows that NTFL incorporates into the sperm head.

Figure 8:
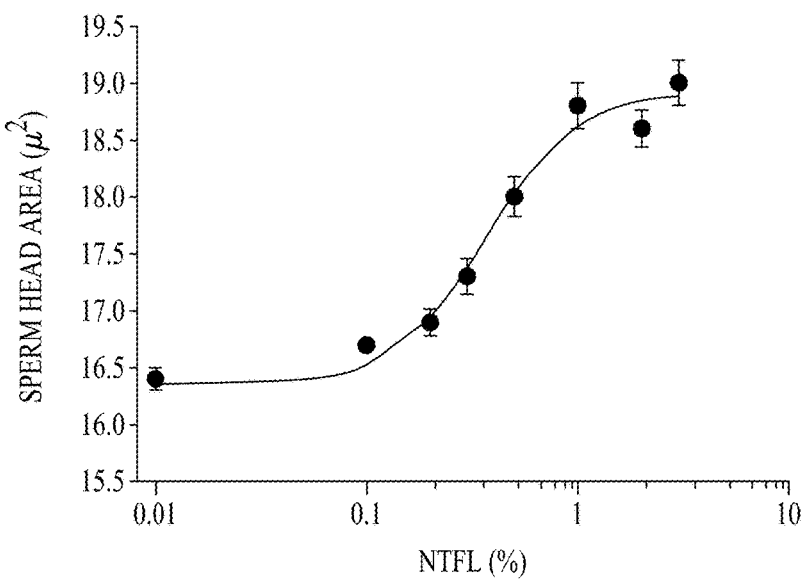
FIG. 8 is a semi-log graph illustrating the increase in sperm head area as a function of NTFL for concentrations up to about 2%.

FIG. 8 is a graph (semi-log) illustrating the increase in sperm head area as a function of NTFL solution concentrations for concentrations up to about 2% in the solution showing that sperm head area increases as the concentration increases.

FIG. 9A is a pie chart and FIG. 9B is a 3 dimensional bar chart illustrating the effect of a 0.1 NTFL solution on a centrifuged sample of sperm. Recognizing that NTFL incorporates into the sperm head, the interference resulting from the presence of micelles was reduced by preparing centrifuged sperm samples to separate the sperm from the lipid micelles. At lower NTFL concentrations the velocities of all sperm were found to be increased. Separation of the sperm cells from the lipid micelles by low speed centrifugation made the enhanced motility of sperm cells by the presence of even a small amount of NTFL more obvious. In addition, sonication and micro-emulsification of NTFL, showed significantly improvement at NTFL concentrations between 0.01 to 0.3%.

FIG. 10 is a Table illustrating the sperm velocity characteristics of the centrifuged sperm samples after exposure to the 0.1% NTFL. While centrifuging enhanced the characteristics of the Control sample, ALH and BCF are still increased by exposure to 0.1% NTFL centrifuged sperm samples, showing its usefulness at these concentrations to promote hyperactivated states (increase of BCF), which is associated with better fertility and healthier sperm. This effect is even more pronounced in the fastest spermatozoa, meaning that the presence of NTFL improves all sperm but is even more effective on the fastest spermatozoa which are the best sperm for causing egg fertilization.

Figure 11A:
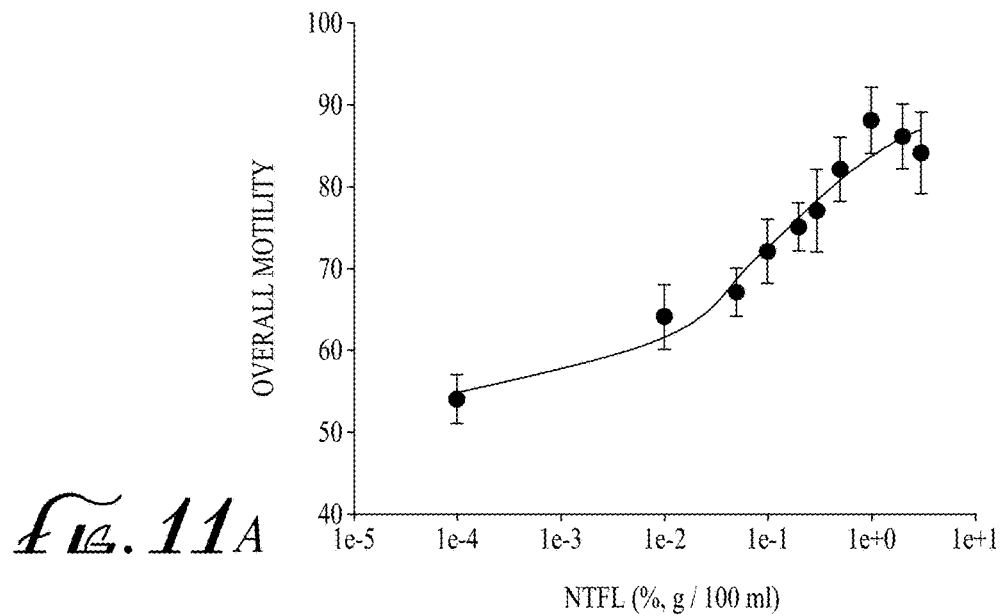
FIGS. 11A and 11B are graphs showing dose response curves for overall motility and motility of the fastest sperm cells.
Figure 11B:
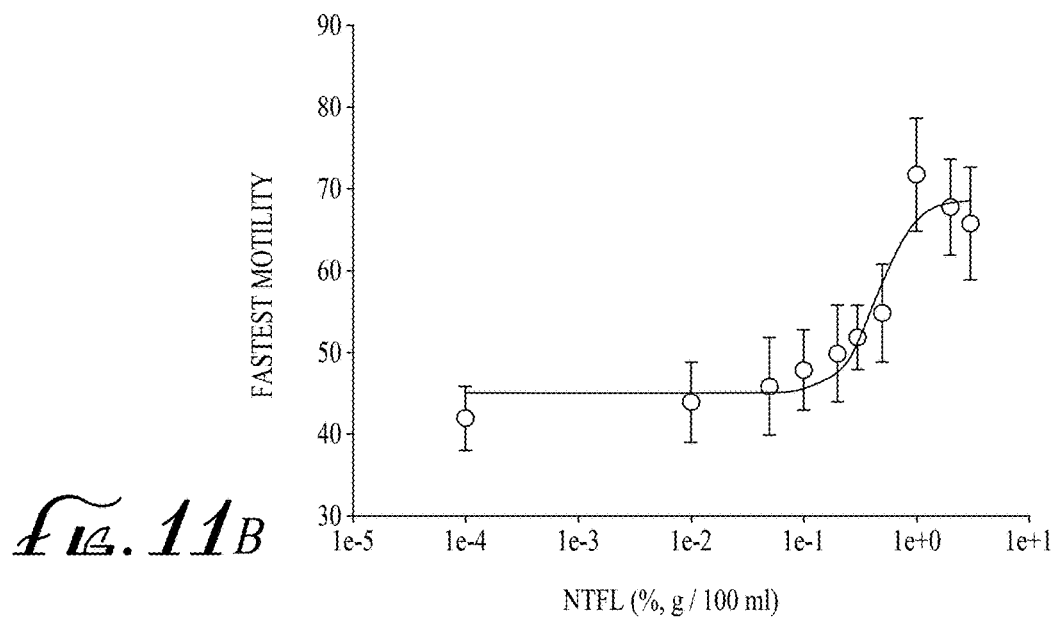

FIGS. 11A and 11B show dose response curves for overall motility and motility of the fastest sperm cells. Both velocities are increased upon centrifugation. However, at concentrations approaching 1% there is a tendency for a reduction in motility because of micelle interference and the head is probably too heavy for the flagella to properly function. The effect is more pronounced and has an IC50 of approximately 0.5% for the fastest sperm compared with overall motile sperm. When cells were separated from the lipid micelles by low speed centrifugation, the enhanced motility of sperm cells was more obvious for overall and fastest motility, with increasing NTFL concentration.

Figure 13B:
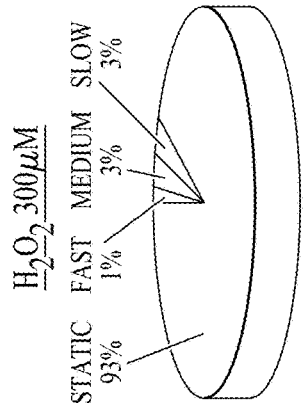
FIGS. 13A and 13B are pie charts illustrating the effect of oxidation on sperm motility.
Figure 13D:
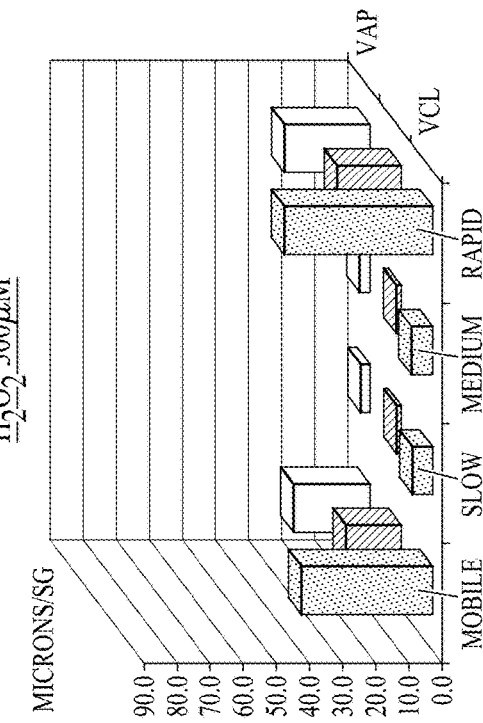
FIGS. 13C and 13D are 3-dimensional bar charts also illustrating the effect of oxidation on sperm motility.
Figure 13A:
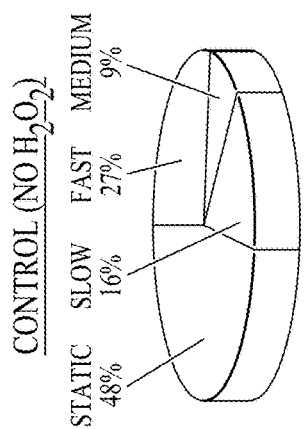
Figure 13C:
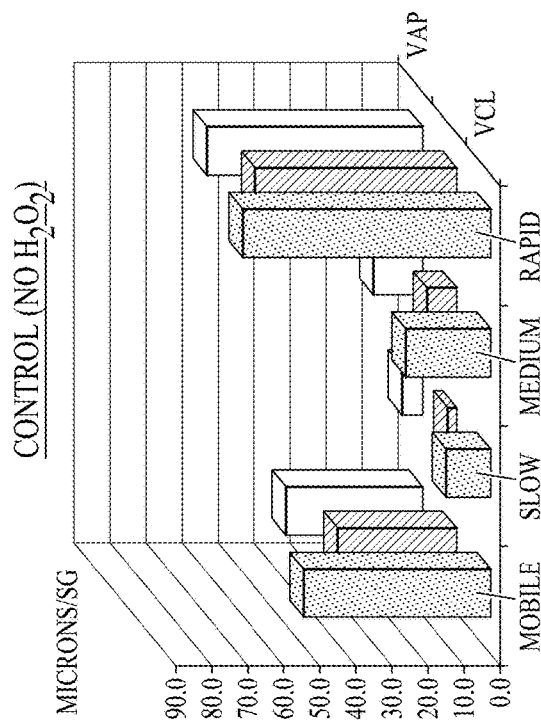

FIGS. 12A, 12B, 12C, 12D, 13A, 13B, 13C and 13D illustrate the effect of low temperature or oxidation respectively on sperm motility. Increasing oxidative stress with hydrogen peroxide or stress by physical means, such as lowering temperatures, decreases sperm motility, and thus all sperm velocities were reduced (FIGS. 13A and 13B). Also, the fraction of static or non-mobile spermatozoa was increased.

FIGS. 14A, 14B, 14C and 14D show that exposure to 0.3% NTFL ameliorates the reduction of motility caused by exposure to lower temperatures or exposure to $H_2O_2$, illustrating that NTFL is also an effective agent to protect spermatozoa against oxidative damage, which is one of the primary causes of male infertility.

Based on the data set forth in FIGS. 1-14A-D and discussed above it is concluded that the motility and capacity of active sperm in the semen obtained from healthy donors is improved by exposure to NTFL. Although the benefits of using concentrations of NTFL near 1% are not readily seen without centrifugation to remove large NTFL micelles that result in collisions with sperm, exposure of sperm to NTFL concentrations below 1% were shown to be real and reproducible. Motile sperm exposed to NTFL had an average increase in sperm velocity parameters (VCL, VSL, VAP, LIN, STR, WOB) of 18.4%. Sperm motility parameters related to flagella activity, which is an indication of the ability to penetrate ovum during fertilization, were also increased by approximately the same degree (ALH and BCF).

Confirming that the NTFL was incorporated into sperm membranes was shown by the increase in sperm head size (increase in sperm head membrane area) during incubation with NTFL. The average size of the sperm heads increased with NTFL concentrations, from an average of 16 um to 19 um. When sperm cells were separated from the lipid micelles by low speed (about 500-1000 RPM) centrifugation, the enhanced motility of the sperm cells was more obvious in the overall sperm population.

Dose-response curves for overall motility effects showed an IC50 of approx. 0.5%, with motility increments with exposure to 0.1%-0.3% NTFL. Even under stress produced by low temperature or oxidation (hydrogen peroxide) exposures, swim-up results obtained for sperm exposed to a 0.1% NTFL solution maintained overall motility and the velocities and flagella assessment showed increases of about 20% for the highly motile sperm which comprises the sperm population primarily responsible for fertilization.

For the data set forth in Examples below and shown in FIGS. 15-24 mature human spermatozoa were obtained by ejaculation from young males of reproductive age (range, 27-39 years). Once obtained, semen was subject to liquefaction for 30 min, followed by a standard swim-up protocol in accordance with standard procedures to enrich the preparation in healthy spermatozoa (Ragni G, De Lauretis L, D'Ambrogio G, Pellegrini S, Maggioni P, Vegetti W, et al. "Semen Preparation By Standard Swim-Up Versus Swim-Up With Test Yolk Buffer Incubation In Intrauterine Insemination: A Randomized Study". *Human Reproduction.*; 13(7):pp 1859-63 (1998)). The isolated spermatozoa were centrifuged at 300×g for 5-10 min, and resuspended in HAM-F10 medium at an approximate concentration of 20-30×10$^6$ sperm/ml. Spermatozoa selected by the swim-up procedure were placed in a sterile incubator at 37° C. and 5% $CO_2$. The selected sperm preparations were incubated under various different conditions for an average time of 2-3 h.

GPLs in physiological solutions spontaneously form bilayers or micelles. Ultrasonicated GPLs at low concentrations tend to form smaller micelles in the diameter range of nm- or sub-mm-sized micelles. Freshly prepared mixtures of GPLs and fatty acids of precise composition, mimicking the GPLs composition for mitochondrial membranes (NTFactor Lipids®, Nutritional Therapeutics, Inc., Hauppuage, N.Y., USA) were used. This mixture of GPLs is known and has proved to be successful for in vivo MLR in several diseases [Nicholsen et al, ibid; Nicolson G L, Rosenblatt S, Ferreira de Mattos G, Settineri R, Breeding P C, Ellithorpe R R, et al. "Clinical Uses of Membrane Lipid Replacement Supplements in Restoring Membrane Function and Reducing Fatigue in Chronic Diseases and Cancer." *Discoveries*, 4(1): e54; Nicolson G L, Ash M E. "Lipid Replacement Therapy: A Natural Medicine Approach To Replacing Damaged Lipids In Cellular Membranes And Organelles And Restoring Function." *Biochimica et biophysica acta*, 1838(6):pp 1657-79; Nicolson G L. "Lipid Replacement Therapy: A Nutraceutical Approach For Reducing Cancer-Associated Fatigue And The Adverse Effects Of Cancer Therapy While Restoring Mitochondrial Function". *Cancer Metastasis Reviews.;* 29(3):pp 543-52.(2010); Nicolson G L. "Mitochondrial Dysfunction And Chronic Disease: Treatment With Natural Supplements" *Alternative Therapies in Health and Medicine;* 20 Suppl 1:pp 18-25; Nicolson G L. "Membrane Lipid Replacement: Clinical Studies Using A Natural Medicine Approach To Restoring Membrane Function And Improving Health". *International Journal of Clinical Medicine*, 7(02): 133 (2016)) but the utility in preserving sperm has not been shown or discussed. The advantage of using a GPL mixture with selected proportions of GPLs and fatty acids is that it mimics the compositions of biological membranes.

Figure 15:
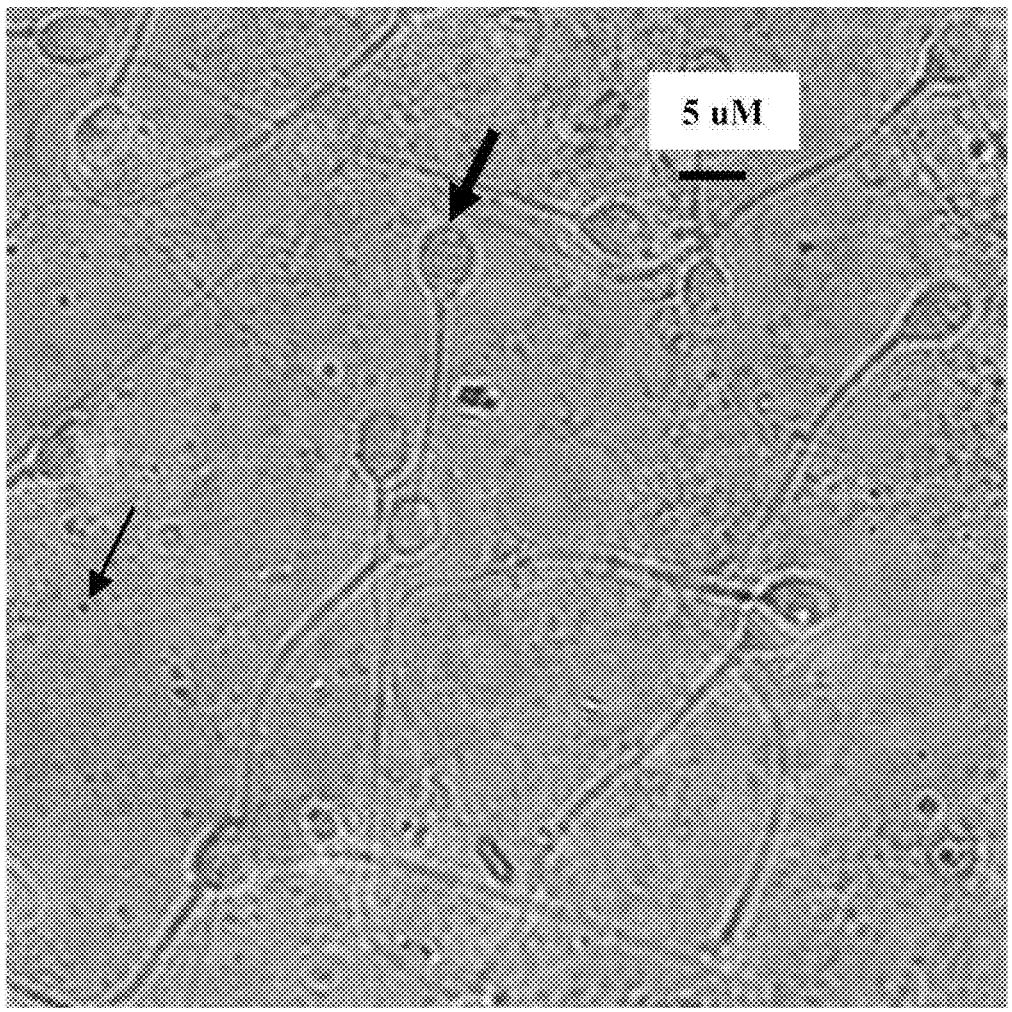
FIG. 15 shows human spermatozoa in an ultrasonicated 3% GPL mixture after a 6-h incubation.

When used in the incubation procedures, the GPLs including inulin were added to the incubation media with less than 0.1% ethanol to enhance solubility. Control incubation medium was HAM-F10. The addition of <0.1% ethanol did not cause significant variations in data (P~0.95, n=8). GPL micelles were prepared at concentrations up to 3% GPL mixtures in the incubation media (typically, 0.1-1% was used) by ultrasonicating the mixture for 15-25 min using a probe sonicator plus a Virtis™ virsonic 475 device (Virtis/SP Industries, Gardiner, N.Y., USA), similar to that reported for the constitution of nanocapsules. The resulting product was purified as sub-µm-sized micelles with a CL-4B Sepharose chromatography size exclusion column. Applying this procedure, sub-µm-sized micelles were obtained that mixed well with the media and that were small enough to be incorporated into the human SM. The incubations were performed in an incubator at 37° C. with 5% $CO_2$, mixing constantly with a shaker inside the incubator, and human spermatozoa were selected by the swim-up procedure for the different experimental conditions. To avoid interference from sub-µm-sized micelles in the measurements of sperm motility, all samples were centrifuged after the incubations at 300 g for 5 min, and the test sperm were taken predominantly from the middle of the centrifugation vial. Centrifugation at low speed does not alter the characteristics of sperm samples. FIG. 15 shows ultrasonicated 3% GPL mixture after a 6-h incubation with human spermatozoa without shaking to enhance the observation of the sub-µm-sized micelles. Nano-micelles rarely exceeded 1 µm in diameter and were usually at the limit of optical resolution (250 nm).

To promote oxidative stress, the incubation was done with 300 µM $H_2O_2$ added to the incubation medium. To evaluate the antioxidant properties of GPL mixtures, sub-µm-sized micelles were added to spermatozoa incubated with or without shaking in HAM-F10 medium with 300 µM $H_2O_2$. FIG. 15 shows precipitated ultra-sonicated sub-µm-sized micelles (thin arrow on the left side of FIG. 15) and human spermatozoa (indicated by the larger, centrally located arrow.

To promote oxidative stress, incubation was done with 300 µM $H_2O_2$ added to HAM-F10. To evaluate the antioxidant properties of GPLs mixtures, sub-µm-sized micelles following the procedure described above, were added to spermatozoa incubated in HAM-F10 with 300 µM $H_2O_2$. A shaker was also used for incubation of the sperm with 300 µM $H_2O_2$.

To observe the direct incorporation of GPLs into SM redox dye Rhodamine 123 was covalently attached to the carboxyl and phosphate residues (especially phosphatidylserine, phospatidic acid and fatty acid components; GPLs like phospatidylcoline react as well). The crosslinking conjugation reaction was elicited with water soluble carbodiimide 1-etil-3-(3-dimetilaminopropil) carbodiimide) (EDC, Thermofisher, USA) under mildly acidic conditions (pH 4-6). The stability of the active ester was improved using N-hydroxysulfoxuccinimide (sulfo-NHS, Thermo Fisher, USA). All of the conjugation reactions were achieved with EDC carbodiimide according to previously publications (Hermanson G T. *Bioconjugate Techniques*; Elsevier Science; 2013; Iwasawa T, Wash P, Gibson C, Rebek J. "Reaction of an Introverted Carboxylic Acid with Carbodiimide. *Tetrahedron*, 63(28), pp 6506-11 (2007) (incorporated herein by reference). The amount and isolation of the Rhodamine 123 crosslinked to the GPLs was evaluated by the procedure of Nakajima et al. ("Mechanism of amide formation by carbodiimide for bioconjugation in aqueous media". *Bioconjugate Chemistry*, 6(1):123-30 (1995) (incorporated herein by reference). The GPL mixture with cross-linked Rhodamine 123 remained fluorescent. To observe the fluorescence of the conjugates, human spermatozoa were incubated with the cross-linked GPL-Rhodamine 123 and then washed using centrifugation and resuspension. This was used solely to test the incorporation of the µm-sized micelles prepared using the GPL mixture-into the sperm membranes, but it was not used for the functional assays described in this paper.

Computer Assisted Sperm Analysis (CASA) was used to test the motility of spermatozoa immediately after the incubation procedure was complete. This was performed with a Microptic™ Sperm Class Analyzer software (SCA) (Microptic, Barcelona, Spain). A volume of 5-15 µl of spermatozoa to be tested for the incubation procedure (concentration 20-40×$10^6$ spermatozoa/ml), were loaded into a Cell-VU sperm counting chamber (Millenium Sciences Inc., NY, N.Y.) and placed on slide warmers at 37° C. Sperm samples in the chambers were observed with a using a 10× phase objective (Nikon Corporation, Tokyo, Japan), with a Basler ACA 780-75GC camera (Basler A G, Ahrensburg, Germany) connected to a computer with the SCA automated software. The acquisition rate to obtain the videos and idealize the trajectories of spermatozoa in the samples was set to 25 frames/sec. For each Cell-VU chamber loaded, the automatic count for the motility parameters used to evaluate a sperm sample to be tested according to WHO standards was set for a minimum of 8-10 different randomly selected microscopic fields (200-500 spermatozoa/field). The values analyzed were total motility (TM, %), progressive motility (PM, %), velocity according to the smoothed path (VAP, µm/s), velocity according to the straight path (VSL, µm/s), velocity according to the actual path (VCL, µm/s), amplitude of lateral head displacement (ALH, μm), head beat-cross frequency (BCF, Hz), straightness (STR, %) and linearity index (LIN, %). The studies focused on the most significant parameters, namely overall motility, TM, VSL, VCL and VAP for fast, slow and non-progressive spermatozoa (with slow, medium or fast velocities). The procedure was repeated three times at each experimental condition during incubation (control, 0.1-1% GPLs, 300 μM $H_2O_2$, 300 μM $H_2O_2$ plus 0.1-1% GPLs). This analysis was performed for samples from 8 different males to get an estimation of the relative variation of dispersion among the different experiments and samples. The variation coefficients obtained varied from 7 to 28% according to the different WHO velocity motility parameters examined and individuals assayed, and this was consistent several published reports.

Following the motility measurements, the remaining sperm suspension was used for fluorescence measurements to evaluate the MIMP of the samples using redox dye JC-1. In functional mitochondria, a strongly negative MIMP favors the accumulation of the cationic JC-1 probe as an aggregate inside the organelle, yielding red fluorescence. In unhealthy mitochondria, MIMP is less negative and the accumulation of JC-1 into the mitochondria is reduced, favoring its accumulation as a monomer that elicits green fluorescence. A stock solution of 5,5',6,6'-tetra-chloro-1,1', 3,3'-tetraethylben-zimidazolyl-carbocyanine iodide (JC-1, Sigma, USA), was prepared at 1 mg/mL in dimethylsulfoxide (DMSO, D8779, Sigma, USA). The JC-1 stock solution was divided into aliquots and stored at −20° C. One milliliter of the sperm suspension was incubated with JC-1 prepared from the stock solution yielding a final concentration of 2.0 mM. Spermatozoa were loaded with the dye under different experimental conditions in the dark in an incubator for 30-40 min at 37° C. with 5% $CO_2$. After loading, sperm were centrifuged at low speed and then resuspended in solutions under the different experimental conditions. In each sample, it was confirmed that staining with JC-1 was accomplished by removing and observing a small sample volume on a slide using an epifluorescence microscope, exciting the dye with an Argon laser at 488 nm. The remaining volume from the samples was analyzed using a FACSCalibur™ Flow Cytometer (Becton Dickinson, Mountain View, Calif., USA) with the CELLQuest software (Becton Dickinson). Forward scatter (FSC) and side scatter (SSC) of the human spermatozoa samples was also determined. The FSC and SSC regions corresponding to the JC-1 stained spermatozoa were determined for acquisition of normal spermatozoa. Samples in the flow cytometer were analyzed to obtain at least 10,000 events for each sample. The samples were excited at 488 nm and emitted light was collected with emission filters at 530 nm (green fluorescence: FL1, dye monomers) and at 585 nm (red fluorescence: FL2, dye aggregates). The values of the photomultiplier were set for logarithmic scale. The ratio of red/green fluorescence is linearly related to the mitochondrial membrane potential. The larger the red-to-green fluorescent ratio, the more negative the average MIMP, which translates to more active and healthier (functional) mitochondria. Dead/live spermatozoa ratios were determined using 10 μg/ml propidium iodide (PI) from a stock solution of 1 mg/ml in water (Sigma Aldrich, USA). PI is a membrane impermeant dye that is generally excluded from viable cells. It binds to double stranded DNA by intercalating between base pairs. It is excited at 488 nm and emits at a maximum wavelength of 617 nm. A negative control of human spermatozoa unstained with the JC-1 dye, was also routinely obtained. The results for each experimental condition were analyzed with FlowJo™ software (FlowJo LLC, Oregon, USA) and displayed either as a dot plot or cytograms of events at green or red wavelength. The GPL mixture used for these experiments was prepared as described above, without covalently attached Rhodamine 123.

The samples of human spermatozoa incubated under different experimental conditions were loaded with JC-1 or Rhodamine 123 redox dyes to evaluate MIMP. The fluorescence intensity of Rhodamine 123 excited at 488 nm and with an emission at 530 nm is linearly related to the MIMP. The stronger the fluorescent signal at this wavelength, the more negative the MIMP. JC-1 was also used as a redox dye to evaluate MIMP red/green fluorescence ratio. The loading procedure for both dyes was the same, and it was performed as described for the flow cytometry experiments. After loading, washing and resuspension of the spermatozoa, they were immobilized for live cell imaging. To immobilize live human spermatozoa the samples were placed for 15 min on thin coverslips coated with poly-L-Lysine (Sigma Aldrich, USA) in semi-sterile conditions in an incubator at 37° C. and 5% $CO_2$, following the procedure described by Wennemuth et al. (Wennemuth G, Eisoldt S, Bode H P, Renneberg H, Schiemann P J, Aumuller G. "Measurement Of Calcium Influx In Surface-Fixed Single Sperm Cells: Efficiency Of Different Immobilization Methods". *Andrologia.*, 30(3), pp 141-6 (1998)). Coverslips with the samples from each experimental condition were placed in a 35 mm microincubator chamber and held at 37° C. for observation under a Leica™ SP5 confocal microscope (Leica GmbH, Germany). The redox dye Rhodamine 123 was excited with an Argon Laser at 488 nm and the emitted light was collected at 530 nm. JC-1 was excited at 488 nm and the emitted light was collected at both, 530 nm (green fluorescence) and at 585 nm (red fluorescence). Images were obtained with either 40× or 63× oil immersion objective lenses and were acquired in xyt scanning mode at 512×512 pixels. To avoid out-of-focus imaging and collection of light from several planes in the size range of a spermatozoa, the pinhole was usually set at 1.5-2.5 Airy Units. Image processing was done using the Leica LAS AF or LAS X suites (Leica GmbH, Germany) and Image J. The GPLs mixture used for these experiments was prepared as described above.

The data obtained by applying the methods described above to samples of human spermatozoa under the different experimental conditions were imported with Image J (NIH, USA) for image analysis or with Sigmaplot 11™ (Systat Software Inc. USA) for statistical analysis, and average plots and non-linear fitting were obtained. Statistical analyses to test the significance in the differences of the mean for multiple experimental conditions were performed by ANOVA analysis using either Sigmaplot 11 or the SPSS software (IBM, USA). When two experimental conditions were compared, analysis was performed by Student t-tests using the same software packages as described for ANOVA.

Figure 16A:
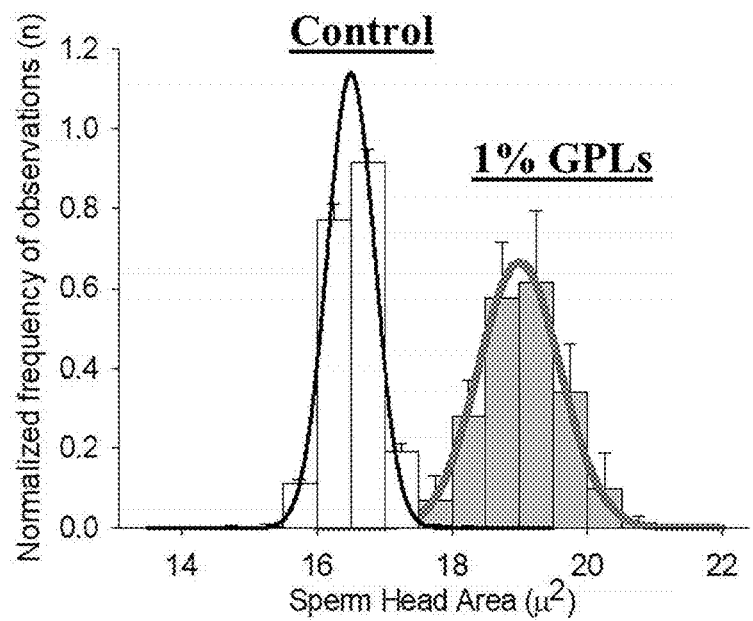
FIG. 16A shows the mean areas of the sperm heads versus the concentration of the GPL mixture in a normalized histograms (FIG. 2A).
Figure 16B:
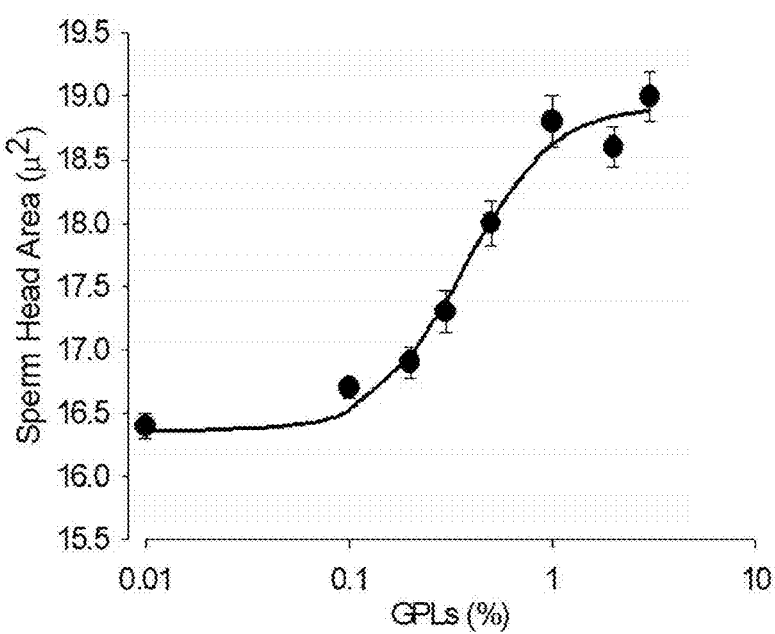
FIG. 16B is a graph showing the size of the sperm head area is dependent on the concentration of GPL.

Ultrasonication of glycerophospholipids creates μm-sized micelles that can incorporate into spermatozoa membranes. When sonicated GPLs were mixed with human sperm, the sperm heads increased in size, evidencing the incorporation of GPLs into the sperm plasma membrane. When the average sperm head area in a control solution was compared to sperm head areas in an ultrasonicated 1% GPL solution, the average area of the sperm heads measured by phase contrast during CASA experiments was significantly greater. The size of the sperm heads increased from an average of 16 μm to 19 μm (p<0.05, independent t-test, n=8). This result held for static or mobile spermatozoa (at all velocities). The GPLs were apparently incorporated into the plasma membrane and other sperm membranes, but this effect was most obvious with the sperm heads. FIGS. 16A and 16B are graphs of the mean areas of the sperm heads versus the concentration of the GPL mixture shown as normalized histograms (FIG. 16A). The size of the sperm head area was dependent on the concentration of GPL (FIG. 16B). Increasing the GPL concentrations enlarged the sperm head area, demonstrating that these variables are related.

Figure 17A:
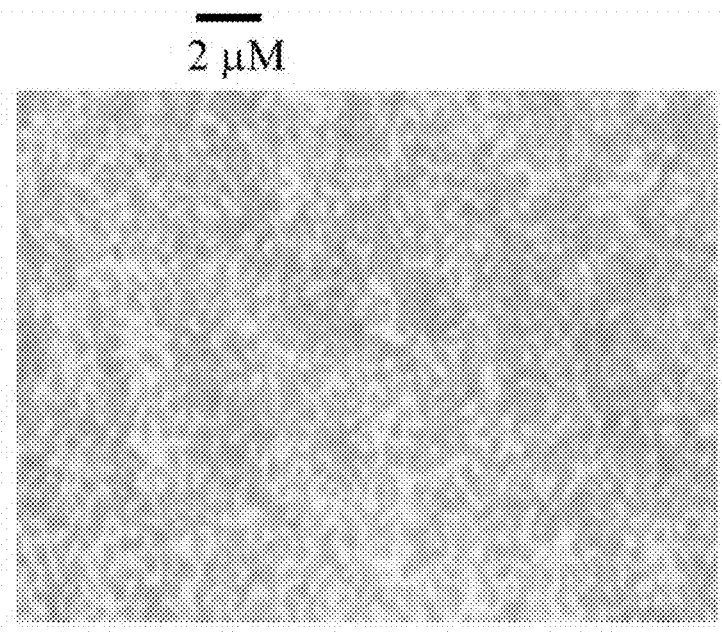
FIG. 17A shows precipitated sub-μm-sized micelles of GPLs crosslinked with Rhodamine 123 and FIG. 17B shows human spermatozoa incubated with sub-μm-sized micelles made of GPLs crosslinked with Rhodamine 123. Images of stained spermatozoa are shown merged with trans-illumination (FIG. 17B, upper) or in fluorescence mode alone (FIG. 17B, lower).
Figure 17B:
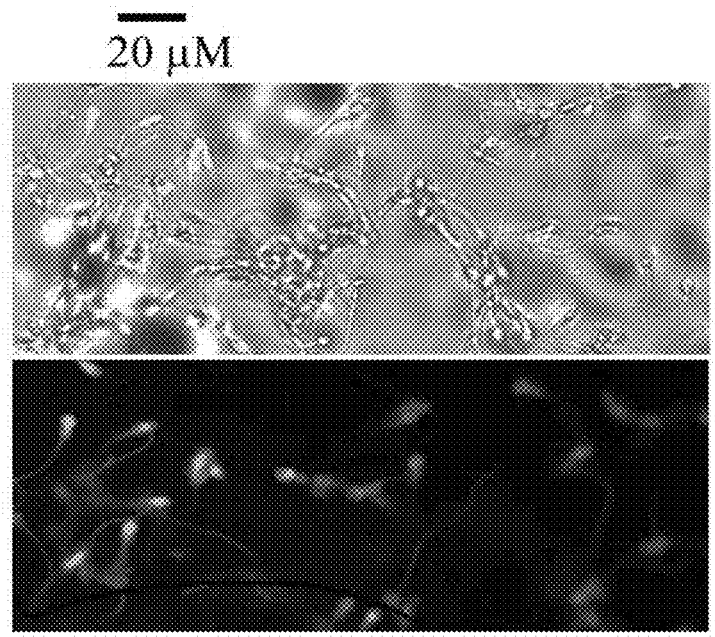

FIGS. 17A and 17B show the sub-μm-sized micelles of 0.1% GPLs crosslinked with Rhodamine 123 in HAM F10 medium. FIG. 17A shows the precipitated μm-sized micelles with the fluorescent dye excited at 488 nm with an Argon Laser at 80% of its maximum intensity. High laser intensities at 488 nm had to be used to get light emission from sub-μm-sized micelles that were not incorporated into biological membranes or the dye alone. This fluorescent bioconjugates were used solely to observe the incorporation of the GPLs into human spermatozoa membranes. Sperm were incubated with a cross-linked GPLs-Rhodamine 123 and then washed using centrifugation and resuspension. The spermatozoa with incorporated, labeled ultrasonicated GPLs are shown in FIG. 17B. Most of the fluorescence is seen in the sperm middle piece and in the sub-equatorial region of the sperm head. This suggests that labeled GPLs in the mixture can incorporate into these regions of the spermatozoa, at least at the level of the plasma membrane. It has been shown that the mitochondrial membranes and the plasma membrane in the mitochondrial sheet around the mid-piece are interrelated and possibly linked, at least transiently.

Figure 18A:
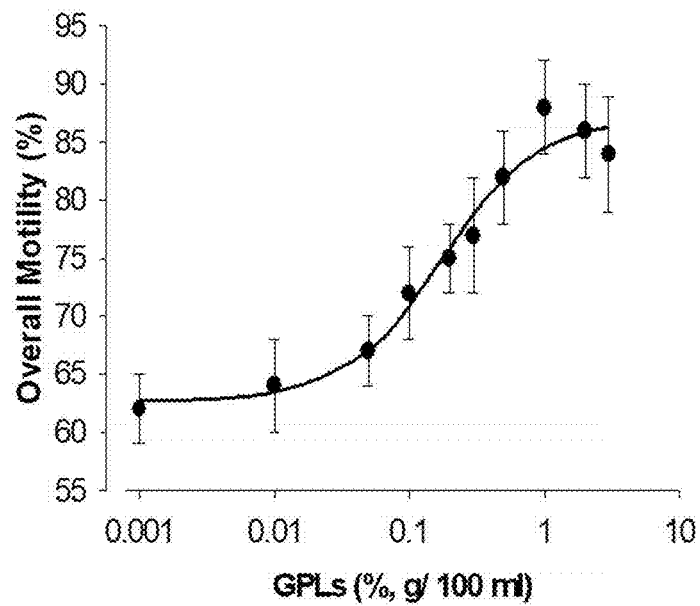
FIGS. 18A and 18B graphically illustrate the results of overall motility and fastest motility versus the concentrations of GPLs.
Figure 18B:
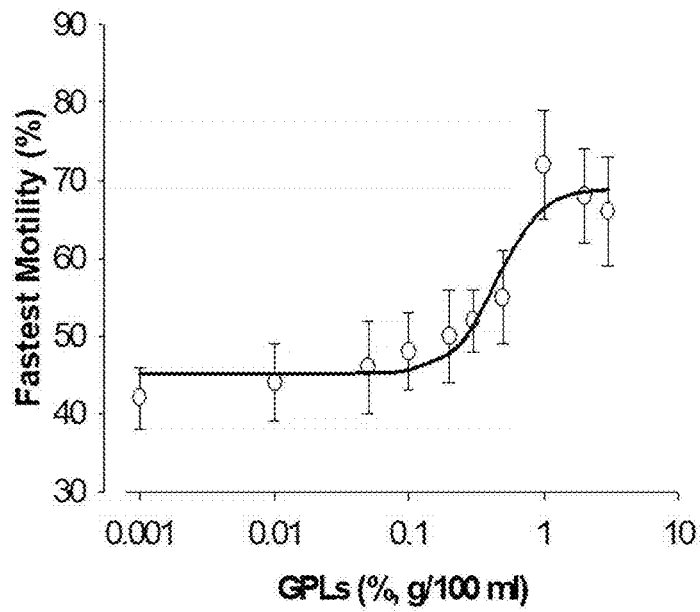

Since the lipid composition of the sperm plasma membrane is a major determinant of sperm motility, it was expected that changes in sperm motility would occur with the incorporation of exogenous GPLs. This is shown by functional data on the incorporation of GPLs from the sub-μm-sized micelles into sperm membranes by measuring the motility of human spermatozoa with Computer Assisted Sperm Analysis (CASA) after incubation of various concentrations of sub-μm-sized micelles made with different concentrations of GPLs. The results of overall motility and fastest motility versus the concentrations of GPLs are shown in FIGS. 18A and 18B. With increasing concentrations of GPLs, both overall motility was increased from 63% to 85% and fastest motility were increased from 45% to 70%. The curve represents the best fit of the Hill equation to the average values of overall and fastest motility observed at each GPL concentration. At concentrations above 1% of the GPL mixture, there was a tendency to observe a reduction in motility because of the size of GPL micelles interfering with spermatozoa displacement, and possibly because the sperm heads became too heavy to sustain motility. If ultrasonication was not done to the GPLs, the micelles also interfered with the normal kinetic movements of the spermatozoa. When spermatozoa were separated from the lipid micelles by low speed centrifugation, the enhanced motility of sperm cells due to the GPL mixtures was more obvious. After incubation and centrifugation at 300-500 g for 10 min at 37° C., the increase in sperm motility can be seen in the GPL-incubated samples, especially at concentrations of GPLs above 0.5%, supporting the findings shown in FIGS. 15 and 16A-B. The data indicate that ultrasonicated GPLs transfer their GPLs into the human SM, modifying their composition and function. Next, MLR was evaluated to determine if the GPLs reduces the damage to SM produced by exposure to oxidizing agents.

FIGS. 18A and 18B are graphs illustrating Dose Response curves of overall motility and fastest sperm motility versus GPL concentration. Both types of velocities are increased by incubation of spermatozoa with sub-μm-sized micelles prepared from GPLs showing a best fit of a Hill equation. FIG. 18B illustrates that the effect is more pronounced ($IC_{50}$ of approximately 0.5%) for the fastest sperm compared with 0.15% for the overall motile sperm shown in FIG. 18A.

Incubation of mature human spermatozoa with an ultrasonicated GPL mixture corrects a decrease in motility resulting from oxidative damage resulting from incubation with hydrogen peroxide. Oxidative stress is major determinant in membrane lipid peroxidation and reduction of sperm motility.

To determine the effect of oxidative stress, sperm motility was measured under four different experimental incubation conditions (control, GPLs, $H_2O_2$, GPLs plus $H_2O_2$). FIGS. 19A-D illustrate the effect on sperm motility using a bar graph (the upper graph in each instance, labeled 19A1-19D1) and three dimensional distribution bar charts of sperm velocities in μm/s using the WHO velocity parameters obtained by CASA under 4 different conditions (lower graph in each instance, labeled 19A2-19D2). FIGS. 19A1 and 19A2 illustrate various sperm criteria under control conditions with no GPL or $H_2O_2$ present. Approximately 52% of the sperm were found to be motile after an incubation period of 3 h in HAM F10 medium. The distribution of velocities for the motile fraction of spermatozoa is also shown in FIG. 19A2. Motile spermatozoa, according to the WHO, can be fast, slow progressive, or non-progressive (and for each speed the front, middle and back bars, respectively illustrate the straight line velocity (VSL), curvilinear velocity (VCL) and average path velocity (VAP)). The plot of velocity versus type of motility for the three spermatozoa velocities, automatically reported by CASA analysis following WHO standards, are shown for a control incubation. Each velocity is indicated (VSL, VCL, VAP) and contains the overall velocity (motile) and the distribution of Fast, Medium or Slow velocities.

The same analysis was performed for spermatozoa incubated 3-4 h in sonicated 0.1% GPLs (FIGS. 19B1 and 19B2). When ultra-sonicated 0.1% GPLs were present during incubation, the overall motility fraction increased from 57 to 68%, and the non-motile spermatozoa decreased from 43 to 32% (n=8, p<0.01). In addition, there was also a statistically significant increase of the fastest motility produced by incubating spermatozoa in sonicated 0.1% GPLs (53% compared to 67%) (n=8 experiments, p, 0.001). The results indicate that incubation in 0.1% GPLs is not detrimental to human spermatozoa, and in fact increases sperm motility. Moreover, this increase is beneficial, as it significantly increased the fastest motility for all velocities examined (VAP, VCL, and VSL). Sperm motility is one of the best indicators of semen quality (Guzick D S, Overstreet J W, Factor-Litvak P, Brazil C K, Nakajima S T, Coutifaris C, et al. "{Sperm Morphology, Motility, And Concentration In Fertile And Infertile Men". *The New England Journal of Medicine*, 345(19), pp 1388-93 (2001).

Oxidative stress was simulated by addition of 300 μM $H_2O_2$ for 3 h to the incubation medium which was found to significantly reduce the motility as monitored by CASA (FIGS. 19C1 and 19C2). Overall motility was reduced to 7% and immotile spermatozoa (non-motile) increased to 93% of the sperm sample. All of the velocities of the various sperm types were dramatically reduced, in agreement with previous reports in the literature. The average sperm velocities diminished dramatically to about 6 μm/s (n=8, p<0.01), with the exception of the fastest velocity sperm (30 μm/s). However, co-incubating the spermatozoa with 300 μM $H_2O_2$ containing additionally 0.1% ultra-sonicated GPLs, not only preserved the motility but increased the overall motility from 5 to 58% and decreased the non-motile sperm from 93% to 42% (n=8 experiments, p<0.01) (FIGS. 19D1 and 19D2). Though all the velocities were increased for each type of motile spermatozoa, the differences were most pronounced for slow and medium velocities (with increases from 6 μm/s to between 10 and 20 μm/s), whereas the fast velocities were increased from 30 μm/s to 42 μm/s (see FIGS. 19D1 and 19D2). These results indicate that ultra-sonicated GPLs can prevent the damage to sperm and sperm motility by agents that promote oxidative stress, such as $H_2O_2$. Thus, exposure to 0.1% GPLs, ameliorates the reduction of motility observed by exposure to $H_2O_2$, showing that the GPL mixture is an effective agent to protect spermatozoa against oxidative damage, which is one of the main causes of infertility.

Figure 20:
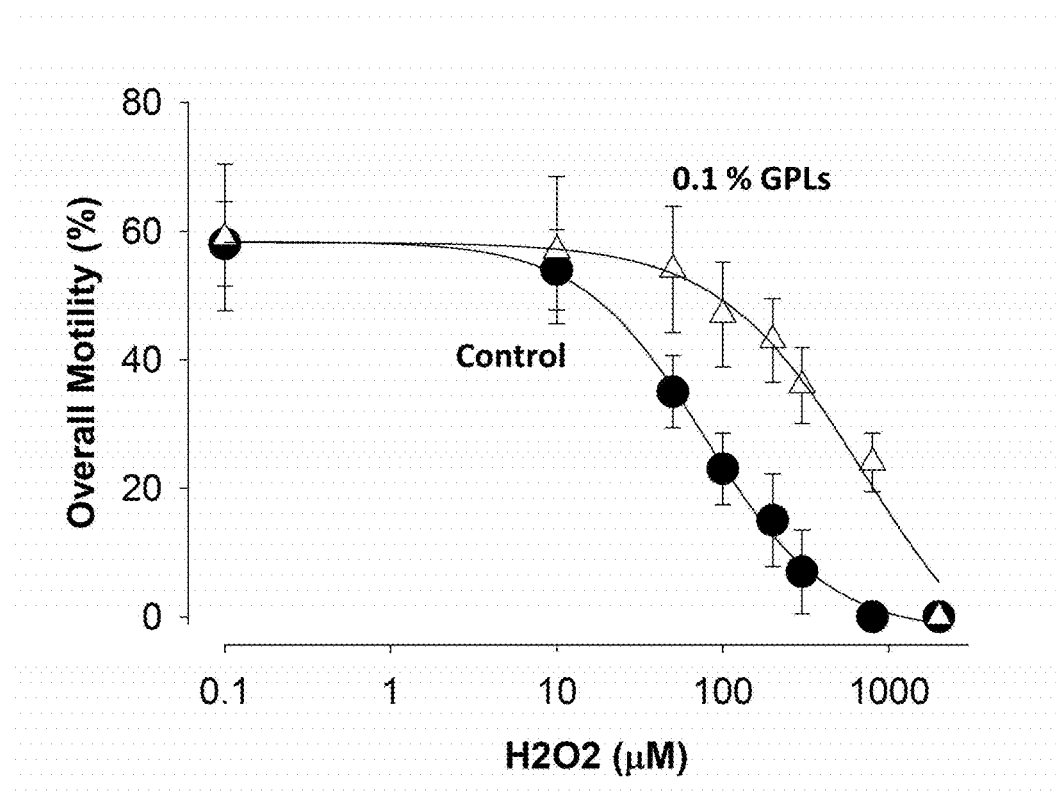
FIG. 20 is a graph showing Dose Response curves of overall motility under increasing concentrations of hydrogen peroxide.

The protective effect of ultra-sonicated 0.1% GPLs on sperm motility when incubated together with different $H_2O_2$ concentrations is also illustrated in FIG. 20 which shows a Dose-Response curve of sperm motility versus increasing $H_2O_2$ concentrations in a control situation versus the improved motility (decreased damage) in the presence of 0.1% GPLs. Overall motility was analyzed after an incubation period of 3 h. The effects of $H_2O_2$ concentrations on overall motility for the control (without GPLs) and for the incubation in 0.1% GPLs are shown. The $IC_{50}$ for overall motility changes from 80±15 to 700±20 μM when 0.1% GPLs are added. The protective effect of GPLs was observed at all concentrations of $H_2O_2$ tested. The results support the protective role of presence of GPLs both in the sperm storage medium as well as absorbed into the sperm head (as illustrated by sperm head size increase) against oxidative stress affecting spermatozoa motility, when they are exposed to different concentrations of $H_2O_2$.

Incubation of mature human spermatozoa with the GPL mixture described herein (NTFL containing inulin) reduces loss of mitochondrial membrane potential promoted by incubation with hydrogen peroxide. Since the viability and motility of spermatozoa are related to the health of their mitochondria (Uribe P, Boguen R, Treulen F, Sanchez R, Villegas J V. "Peroxynitrite-Mediated Nitrosative Stress Decreases Motility And Mitochondrial Membrane Potential In Human Spermatozoa". *Molecular Human Reproduction*, 21(3):pp 237-43 (2015); Amaral S, R S T, Baptista M, Sousa M I, Silva A, Escada-Rebelo S, et al. "Mitochondrial Functionality and Chemical Compound Action on Sperm Function". *Current Medicinal Chemistry;* 23(31), pp 3575-606 (2016)) and because applicants have observed incorporation of GPLs in regions of spermatozoa where mitochondria are abundant, evaluations were conducted to determine if these effects are correlated with mitochondrial function. Further, most of the ROS/RNS damage in spermatozoa is linked to mitochondrial dysfunction. Maintenance of MIMP is directly related to mitochondrial function (Perry S W, Norman J P, Barbieri J, Brown E B, Gelbard H A. "Mitochondrial Membrane Potential Probes And The Proton Gradient: A Practical Usage Guide". *BioTechniques*, 50(2):98-115 (2011). To examine if GPLs can restore mitochondrial function in a population of spermatozoa, flow cytometry of spermatozoa loaded with JC-1, a fluorescent redox dye which is an indicator of MIMP, was performed. Since JC-1 fluorescent ratio at 535/595 nm is directly related to MIMP, the red-to-green dye ratio of JC-1 was examined in a mixture of spermatozoa incubated under various different conditions, namely 0.1% GPLs, 300 μM $H_2O_2$, 300 μM $H_2O_2$ plus 0.1% GPLs and exposure to the toxic agent propidium iodide (PI). JC-1 is a ratiometric dye; the greater the ratio of red vs. green intensities for the cells, the healthier they are, and as the ratio red/green fluorescence increases, the more negative the MIMP, and the more high-energy molecules produced. In other words, healthier cells have a greater red fluorescence.

Figure 21A:
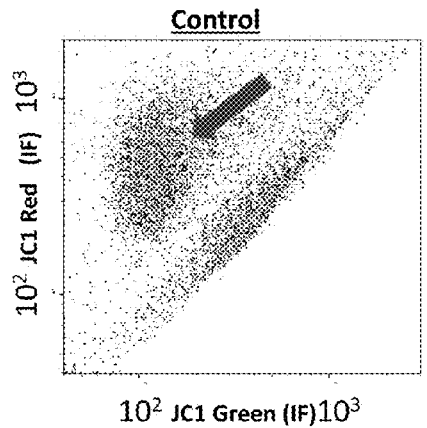
FIGS. 21A-F are dot plots from flow cytometry of spermatozoa loaded with JC-1, a mitochondrial reporter, under different conditions where

FIGS. 21A-21F show, in log-log scale, the red-to-green fluorescence of individual sperm cells under the various treatment conditions. The figures represent the data with dots colored blue, green, and yellow-to-red indicating lower to higher densities/probabilities of the results obtained with spermatozoa for each pair of fluorescence intensities for red and green emission. Higher ratios of red versus green emission indicates healthier spermatozoids, because the distribution reports collectively a more negative MIMP. Two types of data point clouds can be distinguished in each of FIGS. 21A-21F. With reference first to the Control shown in FIG. 21A, a first type of data cloud is found on a diagonal following an almost direct proportional ratio of red-to-green fluorescence with a slope of approximately 1. These spermatozoa are likely to be damaged or at least not in a healthy condition (FIG. 21A). The red arrow indicates another separate cloud of data points with a higher red/green fluorescent ratio, indicating a higher red/green fluorescence ration and functional maintenance of the MIMP and mostly healthy spermatozoa.

Figure 21B:
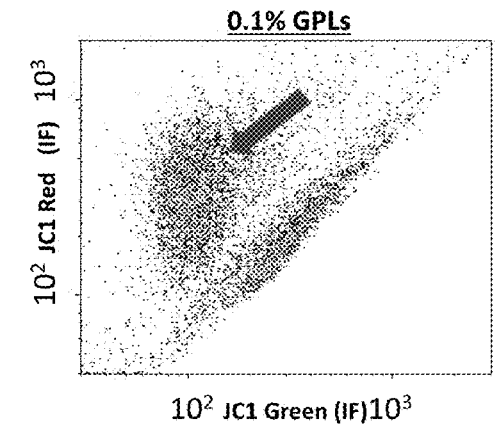
Figure 21C:
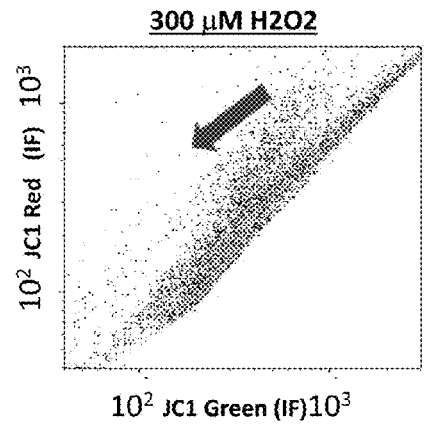
Figure 21D:
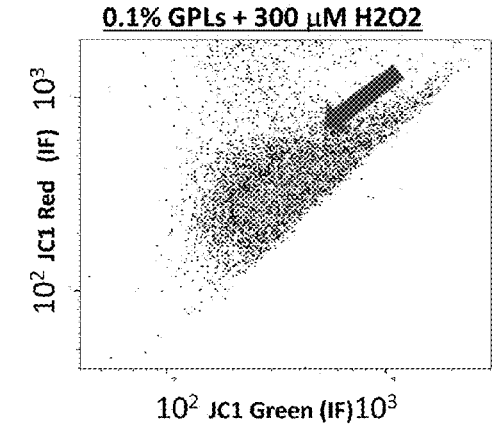
Figure 21E:
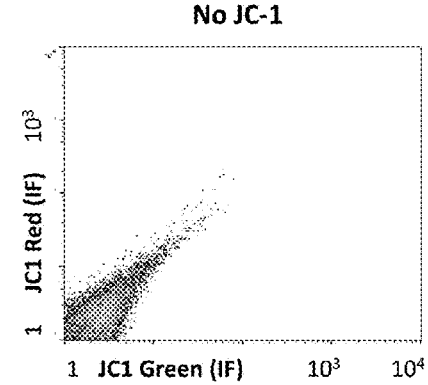
Figure 21F:
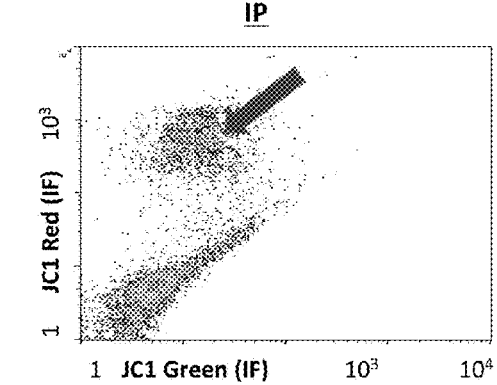

In FIG. 21B illustrates the same test applied spermatozoa incubated with 0.1% GPLs. Since the results are substantially similar to the control in FIG. 21A, GPLs are shown to be non-toxic to the spermatozoa and may even increase slightly their viability as slightly more yellow-red appears. This is apparent because the cloud of healthy spermatozoids in the GPL-treated sample has the same or larger area than that observed in the control, indicating that GPLs treatment can improve the control viability. When spermatozoa were incubated with a toxic oxidizing agent (300 μM $H_2O_2$), the cloud of healthy spermatozoa substantially disappears, and only the diagonal cloud corresponding to non-healthy spermatozoa remains (FIG. 21C). The addition of 0.1% GPLs to the incubation along with 300 μM $H_2O_2$ promotes the appearance of healthy spermatozoa (red arrow, FIG. 21D). This plot is clearly different from FIG. 21C, after incubation with 300 μM $H_2O_2$ alone, suggesting a protective role of GPLs against the loss of MIMP promoted by $H_2O_2$. The plot in FIG. 21E illustrates the control without JC-1 indicating that the low levels of fluorescence shown at the left-bottom of each panel represent nonspecific emission. To evaluate sperm cell viability and membrane integrity, an intercalating fluorescent agent (PI) was applied during the incubation with the JC-1 dye. PI is also toxic to cells, promoting cell death. Although most of the spermatozoa died during the incubation with PI, yielding a pattern similar to non-JC-1-stained spermatozoa, some sperm survived corresponding to the position of the cloud shown in FIGS. 21A-D and indicated by the red arrow.

Flow cytometry fluorescence histograms using JC-1 plot the number of events for red (left graph, FIGS. 22A1-22F1) and green (right graph, FIGS. 22A2-22F2) fluorescent intensities under different experimental conditions for each of FIGS. 22A-F. The area under each curve represents the number of sperm found at different fluorescence intensities (semi-log plot). FIGS. 22A1 and 22A2 shows the control histograms. There is a single red fluorescence peak at with an intensity of 400 arbitrary units (FIG. 22A1, left panel). The range of events is distributed at fluorescence intensities between 100 and 2000 (log scale). In contrast, when 0.1% GPLs are added to the medium, there are two peaks in the green fluorescence histogram (FIG. 22B2), one at 100 and another at 400 arbitrary units. The red-to-green ratio for the lower peak is approximately 4, suggesting that the highest peak at a lower green intensity corresponds to healthy spermatozoa. When comparing the distribution of red versus green fluorescence in both plots, the green fluorescence peak that corresponds to the red fluorescence peak is lower than the other green fluorescence peak, and therefore this lower peak represents unhealthy spermatozoa with lower MIMP.

FIGS. 22B1 and 22B2 show the same results were obtained after incubation of the spermatozoa with 0.1% GPLs. This result indicates that the addition of GLPs does not result in damage to the spermatozoa. FIGS. 22C1 and 22C2 show the results of spermatozoa incubated with 300 µM $H_2O_2$. The red fluorescent intensity is shifted towards lower values with a peak at about 130 arbitrary units, and the green fluorescent intensity becomes one peak centered at about 300 arbitrary units of fluorescence intensity. These results indicate that most of the spermatozoa have a dramatically lower ratio of red/green fluorescence after treatment with $H_2O_2$, suggesting a dramatic loss of MIMP and an increase in unhealthy spermatozoa. FIGS. 22D1 and 22D2 show the effect of adding 0.1% GPLs to the spermatozoa in the presence of 300 µM $H_2O_2$. The peak for red fluorescence is shifted towards 250 fluorescence intensity units, whereas the histogram for green fluorescence reveals a bimodal plot similar to that observed in FIGS. 22A1, 22A2, 22B1 and 22B2. The peak at lower intensity is positioned at about 120 arbitrary units, whereas the peak at higher intensity is positioned at about 300 arbitrary units. The reappearance of two peaks of green fluorescence suggests a protective effect of the GPLs on the mitochondria from the oxidative stress produced by 300 µM $H_2O_2$. FIGS. 22E1 and 22E2 show the control histograms for red and green fluorescence without addition of JC-1. Thus, the fluorescence measured in FIGS. 21A-22F and FIGS. 22A-22D were due to the presence of JC-1 and are not artifacts. In FIGS. 22F1 and 22F2, the histograms are shown after incubation with PI. PI molecules can enter spermatozoa having lost membrane integrity, and are also toxic to spermatozoa. With PI treatment the red fluorescence peak is observed at approximately 700 arbitrary units, corresponding to surviving, viable spermatozoa. The number of events in the vertical axis in FIGS. 22F1 and 22F2 are very low in comparison with FIGS. 22A1-22D1, and the green fluorescence is also low, mostly at intensities below 100, indicating the presence of non-viable spermatozoa after exposure to PI. This control indicates that the results in FIGS. 22A-22D—reflect measurements with viable spermatozoa.

The results of FIGS. 22A-22F supports the conclusion that the incubation of mature human spermatozoa with a GPL mixture provides a beneficial storage environment for spermatozoa and reduces the loss of MIMP caused by oxidation, such as resulting from the presence of hydrogen peroxide. Similar exposures to potential damaging environments were performed using Rhodamine 123 and JC-1, and the sperm were examined under a confocal microscope. The results confirmed the cyotofluorographic studies.

Figure 23A:
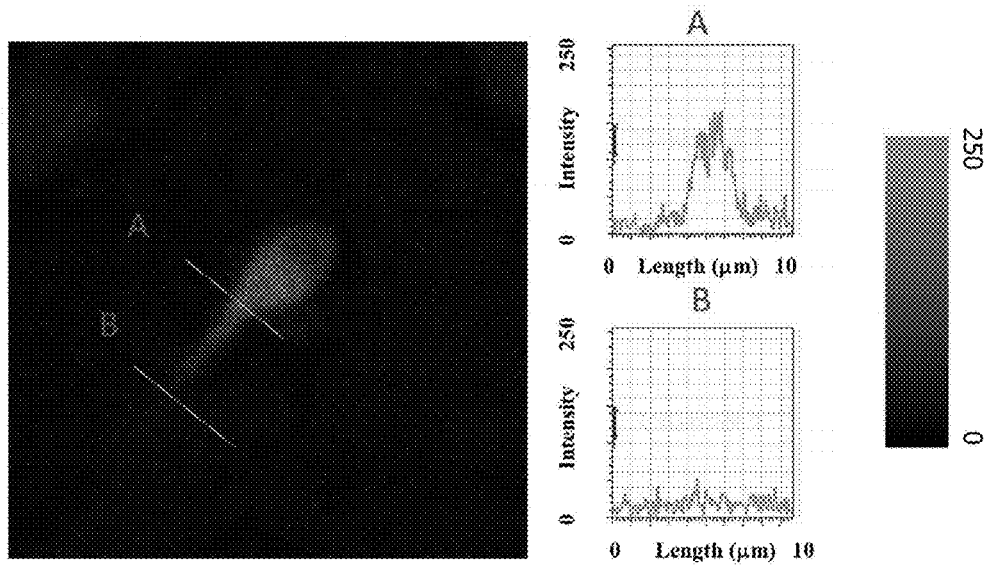
FIGS. 23A-23D are confocal images of human spermatozoa stained with Rhodamine 123 under different experimental conditions. Segments A on FIGS. 23A-23D identifies a portion of the sperm enriched in mitochondria, whereas segmenst B on FIGS. 23A-23D indicate a sector devoid of mitochondria. Fluorescence intensity plots from segments A and B are shown to the right of each of FIGS. 23A-23D for Spermatozoa stained with Rhodamine 123 under control conditions.
Figure 23B:
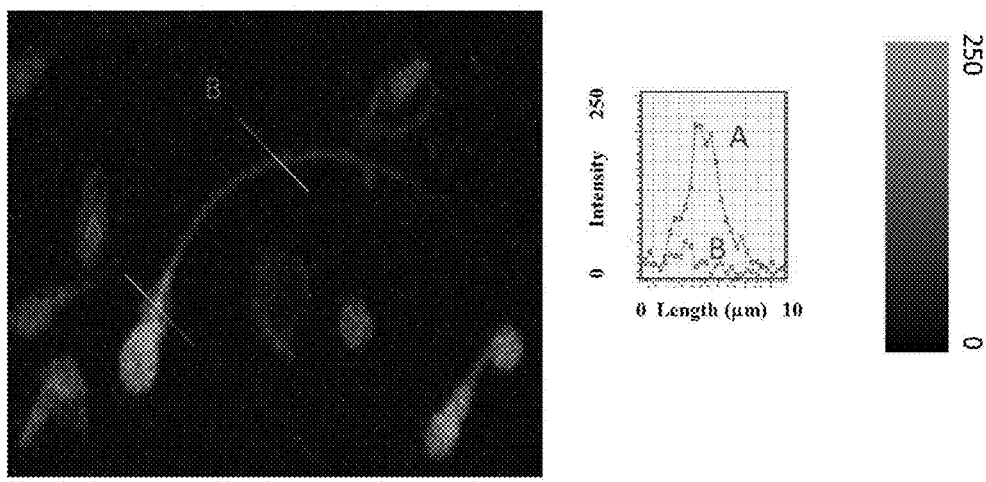

Flow cytometry has the advantage of examining thousands of cells under different experimental conditions, but it cannot evaluate the origin of the fluorescent signal. To better understand this as well as the improvement of viability over time in spermatozoa incubated with GPLs, spermatozoa was examined under a confocal microscope after incubating them with dyes that can evaluate MIMP. FIGS. 23A-23D illustrate spermatozoa incubated with Rhodamine 123 under several different conditions for 3 hours (control, 0.1% GPLs, 300 µM $H_2O_2$ and 0.1% GPLs plus 300 µM $H_2O_2$). After incubation in control media, segment A of the spermatozoa was rich in mitochondria while segment B was devoid of mitochondria, respectively (FIG. 23A). The fluorescence intensity for those sperm segments A and B are shown to the right of the photomicrograph of the sperm image The higher the fluorescent intensity observed in segment A, the healthier the mitochondria. The pseudo-color intensity scale is also shown. The peak of fluorescence intensity in segment A is between 150 and 200. FIG. 23B shows a confocal image of spermatozoa after incubation with 0.1% GPLs and stained with Rhodamine 123. The neck of a spermatozoa (segment A) has an intense fluorescence intensity (peak A, in the graph to the right) compared with other regions of the spermatozoa (such as segment B shown in peak B, in the graph to the right). The fluorescence intensity in the dye-intense regions can reach values of approximately 200 arbitrary units (see color chart to the right of FIG. 22A).

Figure 23C:
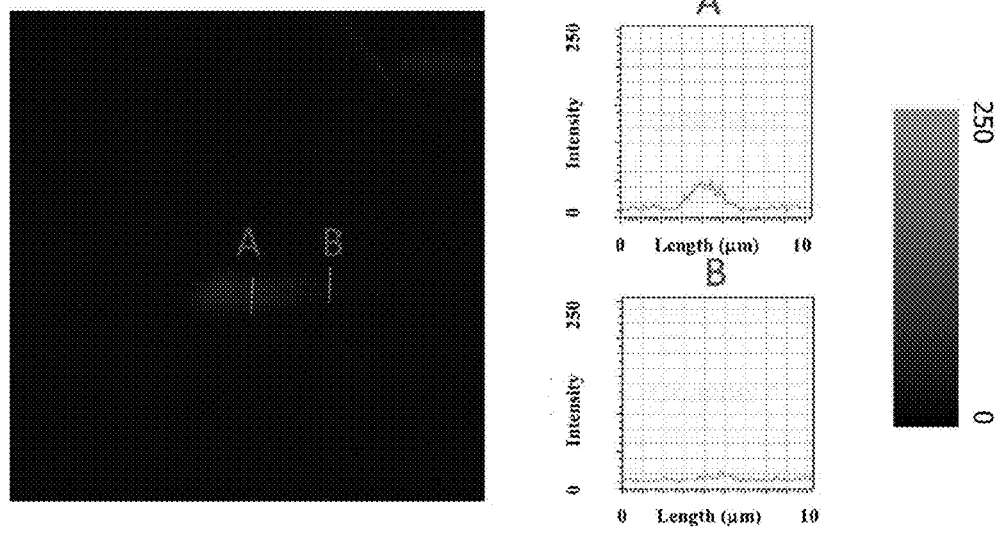
Figure 23D:
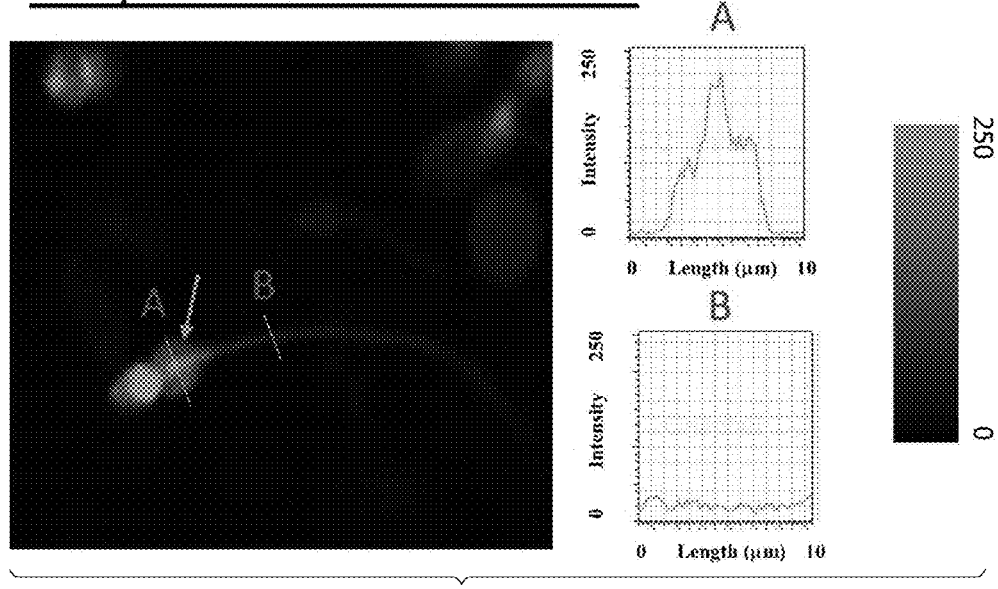

A further discovery is that when spermatozoa are incubated with GLPs, a cytoplasmic droplet appeared in many sperm cells. It appears that such cytoplasmic droplets are indicative of stronger resistance to oxidative and other damaging events. Spermatozoa membrane channels and signaling processes localized in the sperm head are essential for the acrosomal reaction and successful fertilization. In FIG. 23C the results obtained after incubation of spermatozoa in 300 µM $H_2O_2$ are shown. Most of the spermatozoa incubated with Rhodamine 123 showed low fluorescence intensity for segments in the sperm neck (segment A). The maximum values observed were around 50 fluorescence arbitrary units. This reduction shows that exposure to 300 µM results in oxidative stress to mitochondria. The loss of staining suggests that exposure to 300 µM $H_2O_2$ results in unhealthy sperm due to the loss of mitochondrial function. Co-incubation of sperm with GPLs plus 300 µM $H_2O_2$ restores the fluorescence values of segment A to 200 arbitrary units. The peak of fluorescence for segment A was in a similar range to those found in FIGS. 23A and 23B, suggesting a protective role of GPLs for the mitochondrial damage produced by $H_2O_2$. Most of the spermatozoa have cytoplasmic droplets (see light blue arrows in FIG. 23D). It is also hypothesized that the cytoplasmic droplet appears as a response to environmental stress. The results under confocal microscopy obtained with Rhodamine 123 under the same conditions as described in FIGS. 21 and 22 are consistent with the results described previously. This supports that GPLs become incorporate into the spermatozoa membranes and partition into the mitochondria, possibly removing and substituting for peroxidized lipids.

Figure 24A:
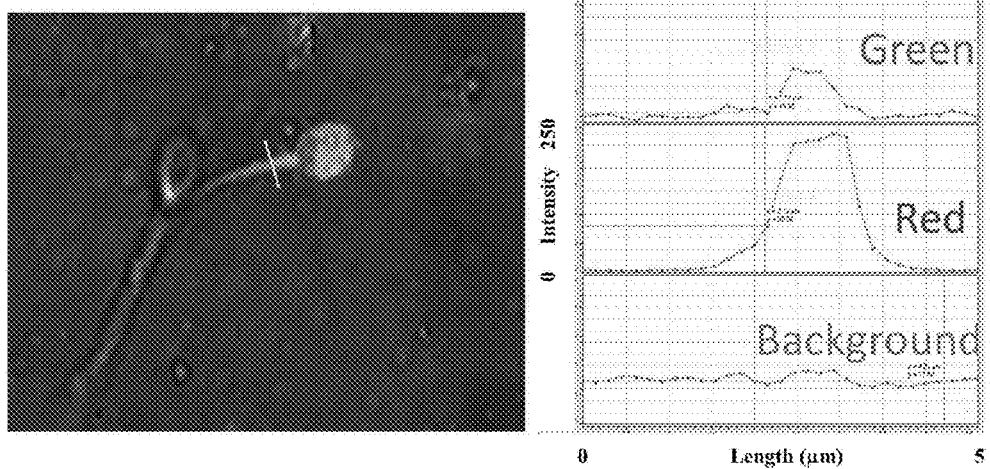
FIGS. 24A-24D are Confocal images of human spermatozoa stained with JC-1 under different experimental conditions where
Figure 24B:
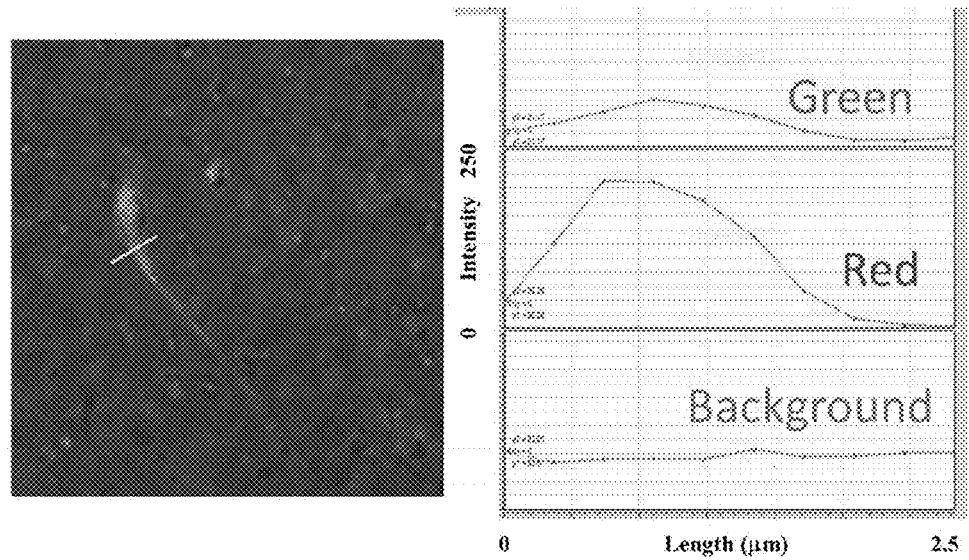
Figure 24C:
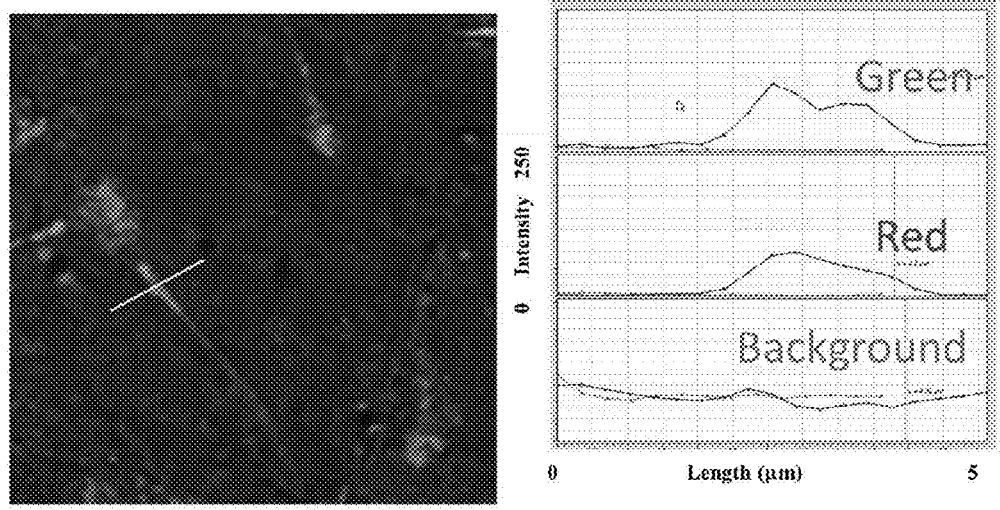
Figure 24D:
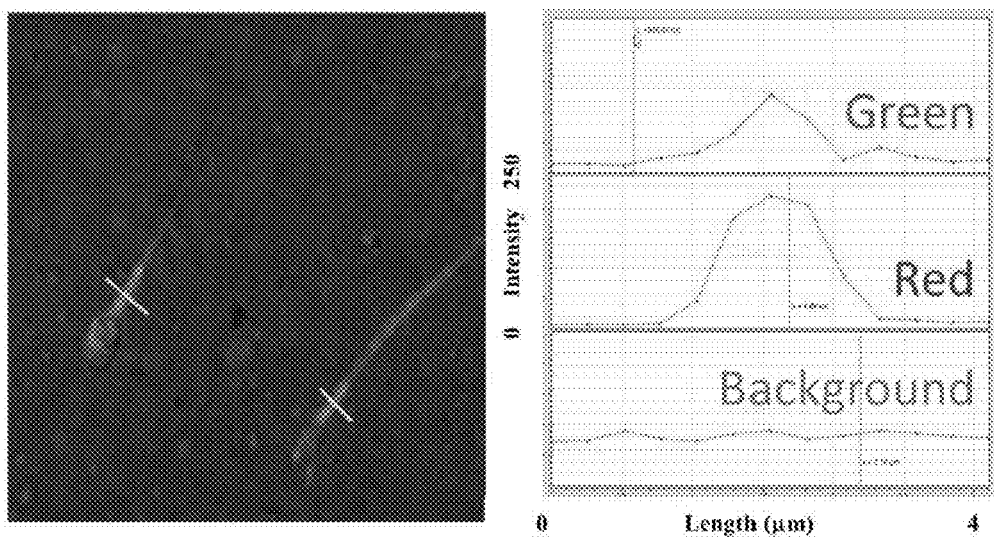

To better assess the MIMP and fluorescence in different sperm segments, such as the neck/midpiece, JC-1 was used instead of Rhodamine 123. Images were acquired at low magnification to evaluate multiple spermatozoa at the same time (FIGS. 24A-24D). This approach was applied to approximately 100 spermatozoa in different fields. Using JC-1, the red/green ratio of the peak signal at the midpiece (represented by the yellow lines) was calculated to obtain an estimation of MIMP and thus the health of spermatozoa. The plots to the right of each of FIGS. 24A-24D (labeled as Green, Red and Background) represent the levels of fluorescence intensity along the yellow segment through spermatozoa. The red/green ratio was almost 2.5±0.1 for the control, indicating that mitochondria stained with JC-1 show negative MIMPs (<−100 mV) (n=16, p<0.01) (FIG. 24A). This same type of experiment was performed in the presence of 0.1% GPLs, yielding a ratio of 2.6±0.15 (n=14, p<0.01) (FIG. 24B). The ratio red/green fluorescence was similar but showed a slight improvement to that seen in FIG. 24A. The incubation in 300 uM $H_2O_2$ causes mitochondrial damage and loss of the MIMPs to less than −50 mV (FIG. 24C). The ratio red/green falls to approximately 0.62±0.12 (n=10, p<0.01). FIG. 24D shows that the addition of 0.1% GPLs to the incubation with 300 µM $H_2O_2$, restored at least partially, the red/green ratio to 1.7±0.18 (n=16, p<0.01). This result is consistent with a protective effect of GPL against mitochondrial oxidative damage. Again, these experiments agree with the conclusion that the GPLs have a protective effect against mitochondrial damage promoted by $H_2O_2$.

Discussion

Membrane Lipid Replacement (MLR) is used to substitute and remove damaged GPLs from cellular membranes in order to modify cellular function. Applicants have found that MLR is useful in ameliorating the symptoms of many chronic diseases, such as fibromyalgia, chronic fatigue syndrome, and metabolic diseases, among others. The data reported herein supports the conclusion that GPLs can be substituted for damaged GPLs in biological membranes to restore mitochondrial function. Damage in biological membranes occurs naturally during cell aging and is increased in pathological conditions. Mitochondrial membranes are especially susceptible to oxidative damage and are relevant targets in these processes. They are also an important source of ROS/RNS, which in turn are a leading cause of membrane lipid peroxidation. Applicant have demonstrated by indirect evidence that MLR can replace damaged lipids not only in the plasma membrane, but also in mitochondrial membranes (Nicolson G L, Ellithorpe R. "Lipid Replacement And Antioxidant Nutritional Therapy For Restoring Mitochondrial Function And Reducing Fatigue In Chronic Fatigue Syndrome And Other Fatiguing Illnesses". *Journal of Chronic Fatigue Syndrome.*, 13(1):pp 57-68, (2006); Flechon J E. "The Acrosome Of Eutherian Mammals". *Cell And Tissue Research.*; 363(1):pp 147-57 (2016); Cuasnicu P S, Da Ros V G, Weigel Munoz M, Cohen D J. "Acrosome Reaction as a Preparation for Gamete Fusion." *Advances In Anatomy, Embryology, And Cell Biology.*; 220:pp 159-72 (2016); Byrne R D, Barona T M, Garnier M, Koster G, Katan M, Poccia D L, et al. "Nuclear Envelope Assembly Is Promoted By Phosphoinositide-Specific Phospholipase C With Selective Recruitment Of Phosphatidylinositol-Enriched Membranes." *The Biochemical Journal.*; 387(Pt 2):pp 393-400. (2005)

Applicants provide herein optical and functional experimental evidence showing the incorporation of GPLs into biological membranes as sub-µm-micelles using human spermatozoa to demonstrate that MLR with GLPs can reduce the functional damage produced by oxidative stress as well as protect and enhance mitochondrial function. The results herein show that incubation of spermatozoa with sub-µm-sized fluorescent-labeled GPL micelles results in incorporation of GPLs into the spermatozoa membranes. In addition, incubation with this GPL mixture reduced the damage of oxidizing agents, such as $H_2O_2$, as evidenced by increased motility of spermatozoa, this increased motility occurring while preventing the loss of MIMP produced by these agents.

Physical evidence of GPLs incorporation into spermatozoa membranes—To test the incorporation of GPLs from the sub-µm-sized GPL micelles into biological membranes spermatozoa was picked as a model cell. Mature human spermatozoa perform all the necessary processes to be able to potentially fertilize female gametes. During maturation sperm cells undergo structural and physiological differentiation of the head, neck, mid-connecting piece and tail regions that prepare them for fertilization. During these critical changes in structure and function, nuclear transcription is absent. It should be noted that the lipid compositions of sperm membranes are constantly modified during maturation, and these changes are crucial for the ability to fertilize an oocyte (Tapia J, Macias-Garcia B, Miro-Moran A, Ortega-Ferrusola C, Salido G, Peña F, et al. "The Membrane Of The Mammalian Spermatozoa: Much More Than An Inert Envelope". *Reproduction in Domestic Animals;* 47(s3), pp 65-75 (2012).

Numerous published articles support the conclusion that sperm motility is critically important for fertilization and is dependent on undamaged membrane lipids and on mitochondrial function, thus supporting the selection of spermatozoa as model cells to directly test MLR and the incorporation of GLPs into their membranes as well as the effects of GLPs on sperm properties important in fertilization. The incubation of the spermatozoa with different concentrations of GPL sub-µm micelles resulted in increases in sperm head thickness and area (see FIG. 16). This lead to the conclusion that GPLs were incorporated into the sperm plasma membranes. To confirm the incorporation of GPLs into sperm head membranes, GPLs were crosslinked with Rhodamine. This procedure had been used previously with liposomes to report lipid incorporation into mitochondrial membranes (Malvezzi H, Sharma R, Agarwal A, Abuzenadah A M, Abu-Elmagd M. "Sperm Quality After Density Gradient Centrifugation With Three Commercially Available Media: A Controlled Trial". *Reproductive Biology And Endocrinology;* 12 (2014) The results confirmed that GPLs from sub-µm micelles can partition into the spermatozoa membranes. Functional evidence was then collected confirming that the sperm had been positively changed by GPL incorporation, such as changes in sperm motility.

Functional evidence of GPL incorporation into spermatozoa membranes—Although there are restricted regions to rapid lateral diffusion in the plasma membranes of spermatozoa there is evidence that exchange of sperm membrane lipids through direct contact and exchange, non-vesicular transport or other pathways of membrane lipid transfer. Thus, the incorporation of GLPs into the sperm plasma membrane results in transfer of these GLPs to the sperm organelle membranes, such as the membranes of mitochondria, residual nuclear envelope (RNE) and the acrosome.

These organelles play important roles in the motility of spermatozoa. Damage to membrane lipids in these organelles and in the plasma membrane have been reported to diminish sperm motility. Hence, it was determined if there were observable changes in basal conditions after incubating spermatozoa with sub-m-sized micelles containing GPL. FIG. 4 examines the result of such an experiment, where incorporating GPL from sub-µm-sized micelles at different concentrations caused different effects. The dual effect on sperm motility by increasing the concentration of GPL was observed. At high GPL concentrations (>3%), the size of micelles started to interfere with the measurements of the motility of spermatozoa, masking some of the results. Even though micelles were separated from sperm in all measurements, a small residual fraction remained. This small fraction became significant at high GPL concentrations, especially at concentrations >3%, interfering with the estimations of sperm motility. At lower concentrations, the size of the micelles did not interfere with the CASA measurements. At these higher concentrations significant increases in sperm motility was observed with the incubation of GPL in sub-µm-sized micelles. The richest areas in phospholipid contents were near the postacrosomal regions around the sperm neck and the RNE.

The RNE is a calcium storage organelle, and it has been implicated as an important source for calcium release in spermatozoa. This is especially relevant because of the possible continuity in sperm membranes and the involvement of the RNE in the process of signaling within spermatozoa. The RNE is also enriched in sterols and phosphoinositosides. These are important signaling molecules that are involved in calcium homeostasis, and they are also critically involved in many essential sperm functions, such as motility, capacitation, acrosome reaction and fertilization. Phosphoinositosides constitute 25% of the GPL mixture. This suggests that MLR can affect or contribute to calcium homeostasis. Moreover, there are several plasma membrane ion channels that have been implicated in the regulation of calcium homeostasis that are modulated by the surrounding lipid environment. For example, CatSper channels are critical for many sperm functions. They are dramatically modulated by progesterone, which in turn is critically dependent on the membrane lipid constitution for its appropriate action. These results suggest several possibilities related to the mechanism of action of MLR, as it suggests that MLR can indirectly affect the functioning of several membrane proteins like ion channels as well as effect intracellular calcium homeostasis.

Protective Role of GPL Against the Loss of Function in Motility Degraded by Oxidative Stress One of the main mechanisms of damage of membrane lipids leading to cell dysfunction is lipid peroxidation. PUFA are especially sensitive to lipid peroxidation. Lipid peroxidation results in several mechanisms that can result in cell dysfunction and death, including the loss of fluidity and organization of the membranes and increased non-specific water permeability of the membrane bilayer.

Compared to other membranes, sperm membranes are particularly enriched in PUFA. For this reason, spermatozoa membranes are particularly susceptible to oxidative stress. In human spermatozoa there are multiple causes for oxidative stress, and such stress has been implicated as a major determinant of male infertility. Therefore, oxidative stress was promoted in spermatozoa by incubating them with $H_2O_2$ and testing to see if the incubation with GPL sub-µm-sized micelles can reduce ROS damage. The functional test was measurement of the motility of human spermatozoa under four different incubation conditions (control, with GPL sub-µm-sized micelles, with $H_2O_2$ and with $H_2O_2$ and plus GPL sub-µm-sized micelles) (FIGS. 19A1-19D2). The fact that motility during co-incubation of $H_2O_2$ plus GLP sub-µm-sized micelles, restores sperm motility to values close to those obtained for the control, suggests that MLR with GPL can prevent the oxidative damage promoted by $H_2O_2$. Oxidative damage promoted by $H_2O_2$ is used as a test to monitor sperm susceptibility to oxidative stress. One of the targets and mechanism of damage of $H_2O_2$ exposure in human spermatozoa is phospholipids. Sub-µm-sized micelles made from fresh GPL mixtures are resistant to peroxidation. A dose-response curve of sperm motility against concentration of $H_2O_2$ with or without GPL sub-µm-sized micelles in the media indicated that the GPL micelles prevented oxidative damage (FIG. 20). The comparison of the dose response curves indicated a shift of the IC50 values of $H_2O_2$, from 80±15 to 700±20 µM, evidencing that protection against oxidative damage by $H_2O_2$ occurred at all doses. These results are consistent with the findings in FIGS. 15-18, suggesting that lipids from sub-µm-sized micelles incorporate into sperm membranes and protect these membranes. Moreover, the data shows that MLR with GPL is also useful for treating those cases of infertility where oxidative damage is increased. As healthy mitochondria are a key to healthy fertile spermatozoa, it was determined if incubation with GPL sub-µm-sized micelles, influences sperm mitochondrial function.

Protective Role of GPLs Against the Loss of MIMP Promoted by Oxidative Stress

Once the added GLP sub-µm-sized micelles contact sperm plasma membranes, they can transfer their constituents directly to sperm. Transfer to internal membranes may also occur via different mechanisms such as non-vesicular lipid exchange and membrane-membrane contact. Nonetheless, liposomes that fuse with the plasma membrane have been used to show translocation of lipids between the mitochondria and the plasma membrane. The endoplasmic reticulum, with functional continuity to the plasma membrane, is a major provider of mitochondrial lipids.

Mitochondria and glycolosis are the main sources of energy production needed for sperm motility. Mitochondria are also one of the main sources of ROS involved in sperm oxidative stress. Excessive ROS production in the mitochondria impact sperm on many cell levels; among them are damage to lipids in the plasma membrane and mitochondrial membranes, resulting in loss of MIMP. An important cellular target of oxidative stress is cardiolipin, a major constituent of the mitochondrial inner membrane. A key precursor of cardiolipin is phosphatidylglycerol, a component of our NTFL mixture. Providing precursors to critical mitochondrial molecules can also be an important element in MLR enhancement in function.

There is also indirect evidence that MLR with GPL can be a useful supplement in many chronic diseases, possibly by replacing damaged lipids in mitochondria. Thus, easy access to the membrane systems in human spermatozoa is a suitable cell model to evaluate whether the loss of MIMP promoted by oxidative stress could be prevented by incubation with NTFL. First MIMP was measured in a large population of sperm using flow cytometry of sperm loaded with the dye JC-1 that reports MIMP. JC-1 reports MIMP by the change of its fluorescence from green to red, depending on its physical state as monomer (green) or oligomer (red). In functional mitochondria, a strongly negative MIMP favors the accumulation of the cationic JC-1 probe as an aggregate inside the organelle, yielding red fluorescence. This is lost in unhealthy mitochondria where MIMP is less negative. In this case, there is less accumulation of JC-1 into the mitochondria as a monomer, resulting in green fluorescence. The incubation of spermatozoa in control and in sub-µm-sized micelles made from a GPL mixture were similar in their dot plots and histograms, suggesting that GPL are not harmful. However, when $H_2O_2$ was added, the dot plots and histogram showed a significant loss of viable sperm cells with an optimal red/green ratio. A situation similar to that obtained for the control was obtained if the incubation with $H_2O_2$ was done simultaneously with the sub-µm-sized micelles made from the GPL mixture. These results support the conclusion that the GPL mixtures can prevent the loss of MIMP produced by $H_2O_2$, and it further suggests that the GPL reaches the mitochondria, replacing the damaged lipids with undamaged ones, restoring MIMP and mitochondrial function. This hypothesis was also tested by observing with a confocal microscope staining in mitochondria after incubating with dyes that report MIMP (Rhodamine 123 and JC-1).

Conclusions

Sub-µm-sized micelles, like liposomes, can fuse with biological membranes and deliver phospholipids that can replace damaged membrane phospholipids in order to restore membrane function. Once in the plasma membrane, these replacement phospholipids can partition or be transferred to other membranes in a cell and restore function. Since this approach does not interfere with other treatment strategies, it can also be used to supplement other pharmacological approaches without the problem of interference or counter-indications that can occur with the use of different drugs.

Human sperm exposed to, or stored in a solution containing an NTFL composition was found to be effective in protecting sperm functionality against damage by physical or oxidative stress. The NTFL composition use is a specific combination of inulin with membrane glycerolphospholipids selected to maintain or enhance the normal sperm cell membrane phospholipid composition. A preferred NTFL composition comprises inulin and a mixture of phospholipids comprising phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid. In a more preferred embodiment for human sperm function preservation, NTFL phospholipid components comprises 19-29% phosphatidylcholine (PC), 15-25% phosphatidylethanolamine (PE), 3.5%-10% phosphatidic acid (PA), 10-18% phosphatidylinositol (PI), 2-10% phosphatidylglycerol (PG), 10-20% glycolipids, and 5-11% other phospholipids. Alternatively, a preferred composition mixture of phospholipids has about 25% to about 29% phosphatidylglycerol (PG), about 68% to about 72% phosphatidylcholine (PC), and up to about 5% phosphatidylethanolamine (PE), and may alternatively comprise about 1% to about 5% phosphatidylinositol (PI) and phosphatidylserine (PS).

Accordingly, since it has been shown that ingestion of NTFL compositions including glycerolphospholipids results in the dissemination and incorporation of the glycerolphospholipids into cellular membranes throughout the body, ingestion of NTFL compositions including phospholipids by a male are likewise expected to result in the incorporation of NTFL phospholipids into sperm cells and the environment where sperm are produced and stored in the body resulting in greater sperm motility in semen.

Further, based thereon it is concluded that exposure of sperm to NTFL compositions including the phospholipids during sperm development and production (spermatogenesis), storage or maturation in males will increase the quality and motility of sperm, and in particular, the quality and motility of the most active and motile fraction of sperm that are most likely to be involved in fertilization. Thus even when the male is considered to be infertile due to lowered sperm motility, or has impaired sperm motility as a result of aging, oxidative stress, variations in ambient temperature or adverse physical conditions, such as elevated inflammation or other conditions, NTFL compositions including phospholipids increase the quality and enhance the motility of ejaculated sperm.

Administering NTFL compositions including phospholipids to a male over a period of time is expected to result in an improvement in the quality of sperm produced by that individual. Administering NTFL compositions including phospholipids to a female over a period of time will likewise enhance the environment in which the sperm is placed and also increase fecundity of the female, thus increasing the likelihood of conception. Thus, the use of NTFL compositions by both males and females further enhance fertility and the likelihood of successful fertilization. It appears that these results can also be applied to mammals and particularly for use in livestock reproduction, such as in bovines, swine and equine by artificial means.

It is further concluded that ingestion, or other forms of delivery of the NTFL composition to a female, for example, using an NTFL containing suppository, by placement of a solution of NTFL within the vagina prior to intercourse or artificial insemination will create an environment for enhanced motility of the sperm subsequently introduced into the vagina.

For example, a fertility enhancing vaginally deliverable NTFL composition can be formed by replacing the nonoxynol-9, or other spermicidal additives with NTFL in vaginal spermicidal creams, jellies, foams, gels, and suppositories or adding NTFL to vaginal lubricants.

Administering NTFL to a male over a period of time will result in an improvement in the quality of sperm produced by that individual, administering NTFL to a female over a period of time will likewise enhance the environment in which the sperm is placed and may also increase fecundity of the female, thus increasing the likelihood of conception, and the use of NTFL compositions by both the male and female will further enhance the likelihood of the sperm fertilizing and oocyte.

We claim:

1. A method of enhancing the health of mammalian spermatozoa and the ability of said mammalian spermatozoa to enhance conception in a female receiving said mammalian spermatozoa for reproduction comprising exposing the mammalian spermatozoa to a prepared aqueous solution of a combination of inulin and phospholipids in an amount effective to increase motility thereof and/or increase the volume of a head portion of the spermatozoa.

2. The method of claim 1 wherein the mixture of phospholipids comprises phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid.

3. The method of claim 1 wherein the phospholipid mixture comprises:
   19-29% phosphatidylcholine (PC),
   15-25% phosphatidylethanolamine (PE),
   3.5%-10% phosphatidic acid (PA),
   10-18% phosphatidylinositol (PI),
   2-10% phosphatidylglycerol (PG),
   10-20% glycolipides and
   5-11% other phospholipids.

4. A method of incorporating phospholipids into membranes of mammalian spermatozoa, enhancing the health of mammalian spermatozoa and enhancing the ability of said mammalian spermatozoa to enhance conception in a female receiving said spermatozoa for reproduction comprising exposing the mammalian spermatozoa to a prepared aqueous solution of a combination of inulin and phospholipids in an amount effective to increase motility thereof, wherein exposure of the mammalian spermatozoa to the effective amount of a combination of inulin and phospholipids results in incorporation of the phospholipids into membranes of the mammalian spermatozoa.

5. A method of repairing or reversing oxidative damage in mammalian spermatozoa, enhancing the health of mammalian spermatozoa and enhancing the ability of said mammalian spermatozoa to enhance conception in a female receiving said spermatozoa for reproduction comprising exposing the mammalian spermatozoa to a prepared aqueous solution of a combination of inulin and phospholipids in an amount effective to increase motility thereof, wherein exposure of the mammalian spermatozoa to the effective amount of a combination of inulin and phospholipids provides repair of, and reversal of, oxidative damage to the mammalian spermatozoa and membranes thereof.

6. The method of claim 4 wherein the mixture of phospholipids comprises phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid.

7. The method of claim 4 wherein the phospholipid mixture comprises:
   19-29% phosphatidylcholine (PC),
   15-25% phosphatidylethanolamine (PE),
   3.5%-10% phosphatidic acid (PA),
   10-18% phosphatidylinositol (PI),
   2-10% phosphatidylglycerol (PG),
   10-20% glycolipids and
   5-11% other phospholipids.

8. The method of claim 5 wherein the mixture of phospholipids comprises phosphatidylglycerol and one or more phospholipids selected from the group consisting of phosphatidylcholine (PC), phosphatidylethanolamine (PE), phosphatidylinositol (PI), and phosphatidylserine (PS), and one or more of linoleic acid (LA) and phosphatidic acid.

9. The method of claim 5 wherein the phospholipid mixture comprises:
   19-29% phosphatidylcholine (PC),
   15-25% phosphatidylethanolamine (PE),
   3.5%-10% phosphatidic acid (PA),
   10-18% phosphatidylinositol (PI),
   2-10% phosphatidylglycerol (PG),
   10-20% glycolipids and
   5-11% other phospholipids.

* * * * *